(12) United States Patent
Sabbadini et al.

(10) Patent No.: US 8,524,484 B2
(45) Date of Patent: *Sep. 3, 2013

(54) IMMUNOGENIC MINICELLS AND METHODS OF USE

(75) Inventors: Roger A. Sabbadini, Lakeside, CA (US); Neil Berkley, San Diego, CA (US); Mark W. Surber, San Diego, CA (US); Matthew J. Giacalone, San Diego, CA (US)

(73) Assignee: Vaxiion Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/412,559

(22) Filed: Mar. 5, 2012

(65) Prior Publication Data

US 2012/0252099 A1 Oct. 4, 2012

Related U.S. Application Data

(60) Division of application No. 12/133,308, filed on Jun. 4, 2008, now Pat. No. 8,129,166, which is a division of application No. 10/832,000, filed on Apr. 26, 2004, now Pat. No. 7,396,822, which is a continuation-in-part of application No. 10/154,951, filed on May 24, 2002, now abandoned.

(60) Provisional application No. 60/359,843, filed on Feb. 25, 2002, provisional application No. 60/293,566, filed on May 24, 2001.

(51) Int. Cl.
C12N 1/21 (2006.01)
C12N 15/00 (2006.01)

(52) U.S. Cl.
USPC ..................................... 435/252.3; 435/320.1

(58) Field of Classification Search
None
See application file for complete search history.

(56) References Cited

U.S. PATENT DOCUMENTS

| | | | |
|---|---|---|---|
| 4,190,495 A | 2/1980 | Curtiss | |
| 4,311,797 A | 1/1982 | Khachatourians | |
| 4,431,740 A | 2/1984 | Bell et al. | |
| 4,732,852 A | 3/1988 | Cohen et al. | |
| 4,782,022 A | 11/1988 | Puhler et al. | |
| 4,895,724 A | 1/1990 | Cardinal et al. | |
| 4,968,619 A | 11/1990 | Curtiss, III | |
| 5,066,596 A | 11/1991 | Manning et al. | |
| 5,338,842 A | 8/1994 | Isberg et al. | |
| 5,744,336 A | 4/1998 | Hodges et al. | |
| 5,808,032 A | 9/1998 | Kurihara et al. | |
| 5,830,710 A | 11/1998 | Progulske-Fox et al. | |
| 5,834,591 A | 11/1998 | Normark et al. | |
| 5,877,159 A | 3/1999 | Powell et al. | |
| 5,888,799 A | 3/1999 | Curtiss | |
| 5,922,583 A | 7/1999 | Morsey | |
| 5,981,182 A | 11/1999 | Jacobs et al. | |
| 6,004,815 A | 12/1999 | Portney et al. | |
| 6,030,805 A | 2/2000 | Normark et al. | |
| 6,080,849 A | 6/2000 | Bermudes et al. | |
| 6,100,066 A | 8/2000 | Potter et al. | |
| 6,143,566 A | 11/2000 | Heintz et al. | |
| 6,150,170 A | 11/2000 | Powell et al. | |
| 6,168,945 B1 | 1/2001 | Sokatch et al. | |
| 6,172,189 B1 | 1/2001 | Devare et al. | |
| 6,248,543 B1 | 6/2001 | de Boer et al. | |
| 6,258,359 B1 | 7/2001 | Labigne et al. | |
| 6,270,776 B1 | 8/2001 | Bloom et al. | |
| 6,291,649 B1 | 9/2001 | Lindberg et al. | |
| 2003/0105310 A1 | 6/2003 | Ashkar | |
| 2003/0166099 A1 | 9/2003 | Sabbadini et al. | |
| 2003/0166279 A1 | 9/2003 | Sabbadini et al. | |
| 2003/0190601 A1 | 10/2003 | Sabbadini et al. | |
| 2003/0190683 A1 | 10/2003 | Sabbadini et al. | |
| 2003/0190749 A1 | 10/2003 | Surber et al. | |
| 2003/0194714 A1 | 10/2003 | Sabbadini et al. | |
| 2003/0194798 A1 | 10/2003 | Surber et al. | |
| 2003/0198995 A1 | 10/2003 | Sabbadini et al. | |
| 2003/0198996 A1 | 10/2003 | Surber et al. | |
| 2003/0199088 A1 | 10/2003 | Sabbadini et al. | |
| 2003/0199089 A1 | 10/2003 | Surber et al. | |
| 2003/0202937 A1 | 10/2003 | Sabbadini et al. | |
| 2003/0203411 A1 | 10/2003 | Sabbadini et al. | |
| 2003/0203481 A1 | 10/2003 | Surber et al. | |
| 2003/0207833 A1 | 11/2003 | Berkley et al. | |
| 2003/0211086 A1 | 11/2003 | Berkley et al. | |
| 2003/0211599 A1 | 11/2003 | Sabbadini et al. | |
| 2003/0219408 A1 | 11/2003 | Sabbadini et al. | |
| 2003/0219888 A1 | 11/2003 | Segall et al. | |
| 2003/0224369 A1 | 12/2003 | Surber et al. | |
| 2003/0224444 A1 | 12/2003 | Sabbadini et al. | |
| 2003/0232335 A1 | 12/2003 | Surber et al. | |
| 2004/0005700 A1 | 1/2004 | Surber et al. | |
| 2006/0002956 A1 | 1/2006 | Surber et al. | |

FOREIGN PATENT DOCUMENTS

| | | |
|---|---|---|
| EP | 2272946 | 1/2011 |
| WO | WO 97/14810 A1 | 4/1997 |
| WO | WO 98/52547 A1 | 11/1998 |
| WO | WO 99/13053 A1 | 3/1999 |

(Continued)

OTHER PUBLICATIONS

Weickert et al., Optimization of heterologous protein production in *Escherichia coli, Current Opinion in Biotechnology*, 7:494-499 (1996).

Ackley, et al., Defensive applications of gene transfer technology in the face of bioterrorism: DNA-based vaccines and immune targeting, *Expert Opin. Biol. Ther.* 3(8):1279-1289 (2003).

Acres et al., Vaccination of Cows with Purified K99 Antigen, K99+ Anucleated Live *E. coli*, and Whole Cell Bacterins Containing Enterotoxigenic *E. coli* for Prevention of Enterotoxigenic Colibacillosis of Calves, *Proceedings of Second International Symposium on Neonatal Diarrhea* pp. 443-456 (1979).

Adler et al., Miniature *Escherichia coli* Cells Deficient in DNA, *Proceedings of the National Academy of Sciences of the United States of America*, 57(2):321-326 (Feb. 15, 1967).

(Continued)

*Primary Examiner* — Nancy T Vogel

(74) *Attorney, Agent, or Firm* — Knobbe Martens Olson & Bear LLP

(57) ABSTRACT

The disclosed invention relates to immunogenic minicells cells (anucleated) and their use to induce an immune response from a subject.

7 Claims, No Drawings

(56) References Cited

FOREIGN PATENT DOCUMENTS

| WO | WO 99/52563 A1 | 10/1999 |
|---|---|---|
| WO | WO 00/09733 A1 | 2/2000 |
| WO | WO 02/072759 | 9/2002 |
| WO | WO 03/033519 A2 | 4/2003 |

OTHER PUBLICATIONS

Barker et al., Isolation by Differential and Zonal Centrifugation of Minicells Segregated by *Escherichia Coli*, *Jo. General Microbiology* 111:387-397 (1979).
Bollen, et al. DNA Transformation Efficiency of Various Bacterial and Yeast Host-Vector Systems *Journal of Clinical Hematology and Oncology* 10:39-48 (1980).
Bonner & Curtiss, *Use of Minicells in Vaccination Against Salmonella Infection*, Abstract (1976).
Botstein, et al. Making Mutations In Vitro and Puttinq Them Back Into Yeast, *Miami Winter Symposia* 19:265-275 (1982).
Bouvier et al., A Gene for a New Lipoprotein in the dapA-purC Interval of the *Escherichia coli* Chromosome, *J. of Bacteriology* 173(17):5523-5531 (1991).
Broach, James R. The Yeast: Plasmid 2u Circle, *The Molecular Biology of the Yeast Saccharomyces: Life Cycle and Inheritance* 445-470 (1981).
Broach, James R. The Yeast: Plasmid 2u Circle *Cell* 28:203-204 (1982).
Brunel et al., Cloning and Expression of *Trypanosoma brucei* kinetoplast DNA in *Escherichia coli*, *Gene* 12:223-234 (1980).
Clark-Curtiss et al., Analysis of Recombinant DNA Using *Escherichia coli* Minicells, *Methods in Enzymology* 101:347-362 (1983).
Courvalin et al., Gene transfer from bacteria to mammalian cells, *C. R. Acad. Sci. Paris, Sciences de la vie/Life sciences* 318:1207-12 (1995).
Coyne & Mendelson, Use of *Bacillus subtilis* Minicells to Demonstrate an Antegenic Relationship Between the Poles and Lateral Cylindrical Regions of Rod-Shaped Cells, *Infection and Immunity* 12:1189-1194 (1975).
Curtiss III, Roy, Genetic Manipulation of Microorganisms: Potential Benefits and Biohazards *Ann. Rev. Microbiol.* 30:507-533 (1976).
Curtiss III, Roy, Research on bacterial conjugation with minicells and minicell-producing *E. coli* strains, *Microbial Drug Resistance* p. 169. Baltimore University Park Press (1976).
de Boer et al., A Division Inhibitor and a Topological Specificity Factor Coded for by the Minicell Locus Determine Proper Placement of the Division Septum in *E. coli* Cell 56:641-649 (1989).
Eck et al., Cloning and characterization of a gene coding for the caterchol 1,2-dioxygenase of *Arthrobacter* sp. mA3 *Gene* 123:87-92 (1993).
Edge, et al., Chemical Synthesis of a human interferon-$\alpha_2$ gene and its expression in *Escherichia coli*, *Nucleic Acids Research* 11(18):6419-6435 (1983).
Eick et al., From initiation to elongation: comparison of transcription by prokaryotic and eukaryotic RNA polymerases, *TIG* 10(8):292-296 (1994).
Fox, et al. Fate of the DNA in Plasmid-Containing *Escherichia coli* Minicells Ingested by Human Neutrophils *Blood* 69(5):1394-1400 (1987).
Frazer et al., Production, Properties and Utility of Bacterial Minicells, 69 *Curr. Top. Microbiol. Immunol.* 69:1-84 (1975).
Gabel et al., The KdpF Subunit s Part of the $K^+$-translocating Kdp Complex of *Escherichia coli* and is Responsible for Stabilization of the Complex in Virtro, *J. Biol. Chem.* 274(53):37901-37907 (1999).
Gemski & Griffin, Isolation and Characterization of Minicell-Producing Mutants of *Shigella* spp, *Infection & Immunity* 30:297-302 (1980).
Giacalone, et al., *Immune responses elicited by bacterial minicells capable of simultaneous DNA and protein antigen delivery*, 24:6009-6017, Aug. 14, 2006.
Grillot-Courvalin et al., Bacteria as gene delivery vectors for mammalian cells, *Current Opinion in Biotechnology* 10:477-481 (1999).

Gyongyossy-Issa et al., Tumour Minicells: Single, Large Vesicles Released From Cultured Mastocytoma Cells, *Tissue & Cell* 17(6):801-809 (1985).
Gyuris, et al., High-Efficiency Transformation of *Saccharomyces cerevisiae* Cells by Bacterial Minicell Protoplast Fusion *Mol. Cell Biol.* 6(9) 3295-97 (1986).
Hanson et al., Molecular cloning, partial purification, and characterization of a haemin-binding lipoprotein from *Haemophilus influenzae* type b, *Molecular Microbiology* 5(2):267-278 (1991).
Harlow et al., Cloning and Characterization of the gsk Gene Encoding Guanosine Kinase of *Escherichia coli*, *J. of Bacteriology* 177(8):2236-2240 (1995).
Hollenberg et al., Mapping of Regions on Cloned *Saccharomyces cerevisiae* 2-um DNA Coding for Polypeptides Synthesized in *Escherichia coli* Minicells, *Molec. Gen. Genet.* 162:23-34 (1978).
Isaacson et al., In Vitro Adhesion of *Escherichia coli* to Porcine Small Intestinal Epithelial Cells: Pili as Adhesive Factors, *Infection and Immunity* 21:392-397 (1978).
Jacobs, et al., Expression of *Mycobacterium leprae* genes from a *Streptococcus mutans* promoter in *Escherichia coli* K-12, *Proc. Natl. Acad. Sci. USA* 83:1926-1930 (1986).
Jannatipour et al., Translocation of *Vibrio harveyi* N,N'-Diacetylchitobiase to the Outer Membrane of *Escherichia coli, J. of Bacteriology* 169(8):3785-3791 (1987).
Kawahara et al., Identification and mappin gof mba regions of the *Salmonella choleraesuis* virulence plasmid of pKDSC50 responsible for mouse bacteremia, *Microbial Pathogenesis* 8:13-21 (1990).
Khachatourians & Berezowsky, Expression of Recombinant DNA Functional Products in *Escherichia coli* Anucleate Minicells, *Biotech. Adv.* 4:75-93 (1986).
Khachatourians et al, A New Method for the Preparation of Minicells for Physiological Studies, *Preparative Biochemistry* 3:291-298 (1973).
Khachatourians et al., Fate of Conjugally Transferred DNA in Minicells of *Escherichia coli* K-12, *Molec. gen. Genet.* 128:23-42 (1974).
Khachatourians et al., *Use of Anucleated Minicells in Vaccination Against Enteropathogenic E. coli*, Abstract 443-455 (1979).
Khachatourians, G., The Use of Anucleated Minicells in Biotechnology: An Overview, *Biotechnology* pp. 309-319 (1985).
Khachatourians, G.G., Minicells as Specialized Vaccine and Vaccine Carriers, *Recombinant DNA Vaccines: Rational and Strategy*, pp. 323-333.
Khachatourians, G.G., The Potential Use of Minicell Cultures in *E. coli* Vaccines, *Proceedings of Minisymposium on Neonatal Diarrhea of Calves and Pigs*, 82-91 (1976).
Khachatourians, G.G., *The Potential Use of Minicell Cultures in E. coli Vaccines*, Calves and Pigs, Veterinary Infectious Disease Organization, University of Saskatchewan, Saskatoon, Saskatchewan, 82-91 (1976).
Kool et al., Proteins Synthesized by a Non-Induced Bacteriocinogenic Factor in Minicells of *Escherichia coli*, *Mole. Gen. Genetics* 115:314-323 (1972).
Kopylova-Sviridova et al., Synthesis of Proteins Coded by Plasmid Vectors of pCV Series ($Ap^r$, $Tc^r$) and their Recombinant Derivatives (pDm) in *E. Coli* Minicells, *Gene* 7:121-139 (1979).
Kozak, Marilyn Initiation of Translation in Prokaryotes and Eukaryotes *Gene* 234:187-208 (1999).
Leung, et al., The yopM Gene of *Yersinia pestis* Encodes a Released Protein Having Homology with the Human Platelet Surface Protein GPIb$\alpha$ *J. of Bacteriology* 4623-4632 (1989).
Lienard et al., Cloning, sequencing and expression of the genes encoding the sodium translocating $N^5$-methyltetrahydromethanopterin: coenzyme M.., *FEBS Letters* 425:204-208 (1998).
MacConnell et al., Expression of FBJ-MSV Oncogene (fos) Product in Bacteria, *Virology* 131:367-374 (1983).
Maniatis, Tom Recombinant DNA Procedures in the Study of Eukaryotic Genes *Cell Biology* 3:563-608 (1980).
Martinez-Salas, et al. Functional Interactions in Internal Translation Initiation Directed by Viral and Cellular IRES Elements *Journal of General Virology* 82:973-984 (2001).

Matsumura et al., Synthesis of mot and che gene products of *Escherichia coli* programmed by hybrid ColE1 plasmids in minicells, *J. Bacteriol.* 132(3):996-1002 (Dec. 1977).

Meagher et al., Protein Expression in *E. coli* Minicells by Recombinant Plasmids, *Cell* 10:521-536 (1977).

Miller et al., Translation in *Escherichia coli* minicells containing Hamster mitochondrial DNA-ColE1 Amp$^r$ Recombinant Plasmids, *Biochemica et Biophysica Acta* 477:323-333 (1977).

Noegel et al., Plasmid Cistrons Controlling Synthesis and Excretion of the Exotoxin α-Haemolysin of *Escherichia coli, Molec. gen. Genet.* 175:343-350 (1979).

Parkhill, et al. Genome Sequence of *Yersina pestis*, the Causative Agent of Plague *Nature Publishing Group* 413:523-527 (2001).

Perry, et al. *Yersinia pestis*—Etiologic Agent of Plague *Clinical Microbiology Reviews* 10:35-66 (1997).

Pickett et al., Cloning, Sequencing, and Expression of the *Escherichia coli* Cytolethal Distending Toxin Genes, *Infection and Immunity* 62(3):1046-1051 (1994).

Purcell et al., Molecular Cloning and Characterization of the 15-Kilodalton Major Immunogen of *Treponema pallidum, Infection and Immunity* 57(12):3708-3714 (1989).

Reeve et al., Minicells of *Bacillus subtilis* A Unique System for Transport Studies, *Biochimica et Biophysica Acta* 352:298-306 (1974).

Roozen et al., Synthesis of Ribonucleic Acid and Protein in Plasmid-Containing Minicells of *Escherichia coli* K-12, *J. of Bacteriology* 107(1):21-33 (1971).

Rosner et al., Expression of a cloned bovine growth hormone gene in *Escherichia coli* minicells, *Can. J. Biochem.* 60:521-524 (1982).

Schaumberg et al., Genetic Mapping of the minB Locus in *Escherichia coli* K-12, *J. of Bacteriology* 153(2):1063-1065 (1983).

Schlosser et al., Subcloning, Nucleotide Sequence, and Expression of *trkG*, a Gene That Encodes an Integral Membrane Protein Involved in Potassium Uptake, *J. of Bacteriology* 173(10):3170-3176 (1991).

Sizemore, et al., Attenuated bacteria as a DNA delivery vehicle for DNA-mediated immunization, *Vaccine* 15(8):804-807 (1997).

Sizemore, et al., Attenuated *Shigella* as a DNA Delivery Vehicle for DNA-Mediated Immunization, *Science* 270:299-302 (1995).

Stieglitz, et al., Cloning, Sequencing, and Expression in Ficoll-Generated Minicells of an *Escherichia coli* Heat-Stable Enterotoxin Gene, *Plasmid* 20:42-53 (1988).

Suzuki et al., Production in *Escherichia coli* of Biologically Active Secretin, a Gastrointestinal Hormone, *Proc. Natl. Acad. Sci. USA* 79:2475-2479 (1982).

Tankersley et al., Induction and Isolation of a Minicell-Producing Strain of *Salmonella typhimurium, Proceedings of the Society for Experimental Biology and Medicine* 145:802-805 (1974).

Zink, Gilbert L. Immunizing Agents and Diagnostic Antigens *Remington's Pharmaceutical Sciences* (73)1324-1340 (1980).

Zubay, Geoffrey, The Isolation and Properties of CAP, the Catabolite Gene Activator, *Methods in Enzymology* 65:856-877 (1980).

Elkins et al. Cloning and constitutive expression of structural genes encoding gonococcal porin protein in *Escherichia coli* and attenuated *Salmonella typhimurium* vaccine strains, *Gene*, 138:43-50 (1994).

Isberg et al. Identification of invasion: a protein that allows enteric bacteria to penetrate cultured mammalian cells, *Cell*, 50:769-776 (1987).

Lee & Isaacson, Expression of the gene cluster associated with the *Escherichia coli* pilus adhsin K99, *Infection and Immunity*, 63(10):4143-4149 (1995).

Nikado, Porins and specific diffusion channels in bacterial outer membrane, *The Journal of Biological Chemistry*, 269(6):3905-3908 (1994).

Rosenshine et al. Tyrosine protein kinas inhibitors block invain-promoted bacteria uptake by epithelial cells, *Infection and Immunity*, 60(6): 2211-2217 (1992).

Scholdel et al. Hybrid Hepatitis B virus Core-Pre-S proteins synthesized in avirulent *Salmonella typhimurium* and *Salmonella typhi* for oral vaccination, *Infection and Immunity*, 62(5):1669-1676 (1994).

Simon & Rest, *Escherichia coli* expressing a *Neisseria gonorrhoeae* opacity-associated outer membrane protein invade human cervical and endometrial epithelial cell lines, *PNAS*, USA, 89:5512-5515 (1992).

Su et al. Construction of stable LamB-Shiga toxin B subunit hybrids: analysis of expression in *Salmonella typhimurium* aroA strains and stimulation of B subunit-specific mucosal and serum antibody responses, *Infection and Immunity*, 60(8):3345-3359 (1992).

Statement of Grounds and Particulars of Opposition dated Mar. 15, 2012 filed in Australian Application No. 2008201082.

Statutory Declaration by Renato Morona (Expert Witness) along with Exhibits RM-1 to RM-6 dated Sep. 13, 2012 and submitted as evidence in support of the Opposition filed in Australian Application No. 2008201082.

IMMUNOGENIC MINICELLS AND METHODS OF USE

RELATED APPLICATIONS

This application is a divisional of U.S. application Ser. No. 12/133,308, filed Jun. 4, 2008, which is a divisional of U.S. application Ser. No. 10/832,000, now U.S. Pat. No. 7,396,822, filed Apr. 26, 2004, which is a continuation-in-part of U.S. application Ser. No. 10/154,951, filed May 24, 2002, now abandoned, which claims priority to U.S. Provisional Application No. 60/359,843, filed Feb. 25, 2002 and U.S. Provisional No. 60/293,566, filed May 24, 2001, all of which are expressly incorporated herein by reference in their entireties.

FIELD OF THE INVENTION

The disclosed invention relates to immunogenic minicells and their use to induce an immune response from a subject.

BACKGROUND OF THE INVENTION

A variety of recombinant protein expression systems have been used to produce immunogenic compositions. Some commonly used expression systems include the rabbit reticulocyte lysate system, *E. coli* S30 Extract System (both available from PROMEGA) (Zubay, Methods Enz. 65:856, 1980), eukaryotic cell culture expression, and bacterial expression systems.

Bacterial expression systems are generally similar to that of the eukaryotic expression systems in that they both use the host cell enzymes to drive protein expression from recombinant expression vectors. In bacterial expression systems, bacterial cells are transformed with expression elements from which transcription is driven. The resulting messenger ribonucleic acid (mRNA) is translated by the host cell, thus yielding a protein of interest.

Bacteria divide very rapidly and are easy to culture; it is relatively easy to produce a large number of bacteria in a short time. Moreover, incorporation of expression elements into bacterial cells is efficient. Cultures of transformed cells can be grown to be genetically identical. Thus, all cells in the culture will contain the expression element.

Bacterial expression systems can be used to produce membrane proteins for use in immunogenic compositions. Although bacterial expression systems can be used to produce antigenic material, there are a variety of disadvantages to use such a system. For example, the potential for contamination of the immunogenic product with live, reproducing bacterial cells renders bacterial expression systems undesirable for producing immunogenic material. Similar drawbacks exist when immunogenic compositions are prepared using eukaryotic host cells.

Minicells produced by host cells are advantageous over whole-cell protein expression systems. Using minicells to produce antigenic compositions greatly reduced the likelihood of contamination with a whole, live cell. Khachatourians (U.S. Pat. No. 4,311,797) exploited an *E. coli* strain that constitutively produced anucleated minicells and constitutively expressed the K99 surface antigen. The resulting *E. coli* derived minicells were prepared as a vaccine. The vaccine induced the production of antibodies against growing and infective enteropathogenic K99+ *E. coli* in cattle and was, thus effective against coniform enteritis. It is important to note that this reference only teaches the use of *E. coli* based minicells to express a naturally occurring *E. coli* gene.

Accordingly, there is still a need in the art to produce immunogenic minicells capable of expressing heterologous genes to stimulate an immunogenic response in a subject. Additionally there is a need to use minicells to carry vectors encoding an antigen of interest that are capable of being expressed in the cells of the target host, and not just in the minicell.

SUMMARY OF THE INVENTION

Embodiments of the invention include methods of generating an immunogenic response in a subject comprising, introducing a minicell to a subject, wherein said minicell comprises a plasmid having an open reading frame encoding an antigen of interest, and a eukaryotic expression sequence operably linked to said open reading frame, such that said antigen of interest is expressed in the subject.

In further embodiments, the plasmid can further comprise a prokaryotic expression sequence operably linked to said open reading frame, such that said antigen of interest is expressed in the minicell and in the subject. In additional embodiments, the antigen of interest expressed in the minicell is displayed on the surface of the minicell.

In more specific embodiments, the eukaryotic expression sequence can comprise a Cytomegalovirus (CMV) promoter. In other aspects, the open reading frame is derived from the genome of a pathogen, including a virus or a bacterium, such as *Bacillus anthracis*, for example. In other aspects, the open reading frame encodes an antigen characteristic of a cancerous cell.

Additional aspects include methods of generating an immunogenic response in a subject comprising, introducing a minicell to a subject, wherein said minicell comprises first and second open reading frames, encoding first and second antigens respectively, and a eukaryotic expression sequence operably linked to said first open reading frame and a prokaryotic expression sequence operably linked to said second open reading frame, such that said first antigen is expressed in the subject, and said second antigen is expressed in the minicell.

In additional aspects, the first and second open reading frames can be located in a plasmid. The first and second open reading frames can be located in the same plasmid or different plasmids.

In more specific embodiments, the eukaryotic expression sequence can comprise a Cytomegalovirus (CMV) promoter. In other aspects, the first open reading frame is derived from the genome of a pathogen, including a virus or a bacterium, such as *Bacillus anthracis*, for example. In other aspects, the first open reading frame encodes an antigen characteristic of a cancerous cell. In specific aspects, the second antigen can be displayed on the surface of the minicell.

Additional embodiments herein include minicells for use in generating an immunogenic response in a subject, comprising a plasmid having an open reading frame, encoding an antigen of interest, and a eukaryotic expression sequence operably linked to said open reading frame, such that said antigen of interest is capable of being expressed in the subject.

In more specific embodiments, the eukaryotic expression sequence comprises a Cytomegalovirus (CMV) promoter. In other aspects, the open reading frame is derived from the genome of a pathogen, including a virus or a bacterium, such as *Bacillus anthracis*, for example. In other aspects, the open reading frame encodes an antigen characteristic of a cancerous cell.

In additional embodiments, the minicells described herein further comprise a prokaryotic expression sequence operably linked to said open reading frame, such that said antigen of interest is capable of being expressed in the minicell and the subject. In advantageous embodiments, the antigen of interest expressed in the minicell is displayed on the surface of the minicell.

DETAILED DESCRIPTION OF THE PREFERRED EMBODIMENT

The disclosed invention relates to the use of minicells for the preparation of immunogenic material. The applications of immunogenic minicells include research, prophylactic, diagnostic and therapeutic applications. The National Institute for Allergy and Infectious Diseases has categorized pathogenic targets for research into three groups, Category A pathogens, Category B pathogens, and Category C pathogens. Any antigen from Categories A, B, and C pathogens can be used with the immunogenic minicells described herein. As an example, the pathogens of Category A, discussed below, provide a number of relevant antigens that can be displayed upon the surface of a minicell in order to use the resulting material as an immunogenic composition effective in protecting subjects from infection of these agents.

In a preferred embodiment, the immunogenic minicells provided herein encode and are capable of expressing a heterologous antigenic product. Accordingly, in more specific embodiments the described minicells can include a vector having a heterologous nucleotide sequence encoding an open reading frame of an antigen of interest. In even more particular embodiments, the immunogenic minicells described herein include vectors having an open reading frame encoding a cancer derived or pathogen derived antigen. As used herein, the term "heterologous" relates to an antigen encoded by the genome of a species other than that from which the minicell is derived. Antigens can be encoded by any suitable species including pathogens, such as viruses, bacteria, fungi, protozoa, and the like. Antigens can also be encoded by human beings and other mammals. This embodiment is particularly advantageous when it is desirable to have minicells displaying a cancer antigen.

Immunogenic Minicells

Minicells can be used to immunize subjects. An organism is "immunized" when it is contacted with an immunogen and the organism produces an immune response to the immunogen. The immune response can be protective or therapeutic. Examples of protective or therapeutic immune responses include the generation of antibodies, such as neutralizing antibodies, or engendering the proliferation or activity of cytotoxic cells against the immunogen.

Immunization strategies can be divided generally into two classes: the use of whole-killed or attenuated pathogens to present immunogens and the isolation of immunogens from a pathogen for use as an immunogen. Presentation of whole-killed or attenuated pathogens has many advantages and frequently produces a robust immune response from an immunized organism.

The use of whole-killed or attenuated pathogens as immunogens, however, has certain risks. Perhaps the most serious of these risks involves the possibility the attenuated immunogen is still sufficiently viable to cause disease in an organism immunized with the attenuated immunogen. Accidental infections with various polio and smallpox vaccines are just two examples of this type of risk.

With the advent of molecular biology techniques it became possible to isolate particular antigens from a pathogen for use in an immunogenic composition. Often these immunogenic compositions comprise a subunit of a pathogen that, when presented to an organism, will permit the immunized organism to generate a protective immune response. One extremely successful example of such a subunit immunogen is the hepatitis B subunit vaccine.

Using an immunogenic composition comprising a subunit of a pathogen is advantageous as it reduces the risk of accidental infection. Unfortunately, isolating one or more subunits from a pathogen for use in an immunogenic composition often leads to a weaker immunogenic composition when compared to a whole-killed or attenuated immunogen. One possible explanation for this phenomenon holds that the isolated and preformed antigenic subunit is altered during production and is no longer in its native confirmation. The resulting immune response to the misshapen immunogen does not serve to prepare a host's immune system to raise a protective immune response against the pathogen of interest.

The use of minicells to present antigens for immunization has several potential advantages. For example, immunogenic minicells are able to present one or more antigenic membrane proteins in their native form to a host's immune system. Native presentation of antigens can be superior to presenting antigens in a non-native form because the immune system response is more likely to recognize an active pathogen based on the prior exposure to the immunogenic minicells.

In addition to the presentation of antigens in their native conformation, immunogenic minicells may present antigens in a manner that more accurately mimics antigen presentation by the active pathogen from which the antigen of interest was derived. For example, most non-enveloped viral pathogens present one or more antigenic epitopes on the surface of their viral coats in a repeating format. It has been theorized that mammalian immune systems have adapted to recognize the presence of repeating antigenic epitopes as the hallmark of an invading viral pathogen. Immunogenic minicells displaying one or more antigens on their surface may be able to more accurately mimic the antigen presentation of a native virus particle and thus elicit a more robust immune response than merely providing an antigen to a host in a non-structured format.

Immunogenic minicells have other advantages over standard immunogenic compositions. Specifically, minicell producing parent cells lines often contain immunogenic components, even in the absence of an antigen of interest being introduced. For example, the lipopolysaccharide component of Gram-negative bacteria is known to be extremely immunogenic. Immunogenic minicells displaying an antigen of interest can possibly elicit a more robust immune response from a host than that elicited by a purified, performed antigen because the host may recognize various components of the minicell as a foreign antigen. As such, immunogenic minicells present both an antigen of interest and an adjuvant to the immune system of a host organism. In addition to native minicell components that may act as adjuvants, the immunogenic minicells disclosed herein may also be altered to include non-native adjuvant molecules that further increase the immunogenicity of the minicell compositions.

In research applications, immunogenic minicells can be used to generate antibodies to an antigen displayed by a minicell. Such antibodies can be used to detect an antigen, which may be a chemical moiety, molecule, virus, organelle, cell, tissue, organ, or organism that one wishes to study. Classically, such antibodies have been prepared by immunizing an animal, often a rat or a rabbit, and collecting antisera therefrom. Molecular biology techniques can be used to prepare antibodies and antibody fragments, as is described elsewhere herein. Single-chain antibody fragments (scFv) may also be identified, purified, and characterized using minicells displaying a membrane protein or membrane bound chimeric soluble protein.

In prophylactic applications, immunogenic minicells are used to stimulate an immune response from a subject. After administration of the immunogenic composition disclosed herein, the subject is "pre-immunized" to a pathogen before contact with the pathogen occurs. This pre-immunization allows the subject to mount a protective immune response to the particular pathogen, thus preventing disease in the subject.

Certain aspects of the invention involve active immunotherapy. Active immunotherapy relies on the in vivo stimulation with an immunogenic composition of the endogenous host immune system. Exemplary immunogenic compositions include immunogens, allergens, toxins, adjuvants, cytokines and chemokines, all of which allow the host immune system to react against pathogens.

Other therapeutic applications involve passive immunotherapy. Passive immunotherapy involves the administration of agents (such as antibodies or effector cells) directed against an immunogen of a pathogen. Passive immunotherapy does not necessarily depend on an intact host immune system. Examples of effector cells include T cells; T lymphocytes, such as CD8+ cytotoxic T lymphocytes and CD4+ T-helper tumor-infiltrating lymphocytes; killer cells, such as Natural Killer (NK) cells and lymphokine-activated killer cells.

Minicell Production

Minicells are anucleated cells that lack chromosomal DNA derived from the minicell producing parent cells from which they are produced. The term "minicells" encompasses derivatives of eubacterial and archaebacterial cells that lack parental chromosomal DNA as well as anucleated derivatives of eukaryotic cells. The immunogenic minicells described herein can be derived from both gram-positive and gram-negative parental cells.

Minicells are produced by minicell producing parent cells. These parent cells undergo cell division in an abnormal manner that produces a chromosomal-containing cell and a minicell lacking a copy of the parental chromosome. Minicells are often smaller than their parent cells. For example, minicells produced from *E. coli* cells are generally spherical in shape and are about 0.1 to about 0.3 um in diameter, whereas whole *E. coli* cells are about from about 1 to about 3 um in diameter and from about 2 to about 10 um in length. Table 1 shows a variety of minicell-producing sources useful in the present invention and discusses the mechanisms by which the minicells are generated.

TABLE 1

Eubacterial Strains, Mutations and Conditions that Promote Minicell Formation

| Species | Strain | Notes | References |
|---|---|---|---|
| *Campylobacter jejuni* | | May occur naturally late in growth cycle | Brock et al., 1987 |
| *Bacillus subtilis* | | Mutations in divIVB locus (inc. minC, minD | Barak et al., 1999 |
| | | ripX mutations | Sciochetti et al., 1999; Lemon et al., 2001 |
| | | smc mutations | Moriya et al., 1998; Britton et al., 1998 |
| | | oriC deletions | Moriya et al., 1997; Hassan et al., 1997 |
| | | prfA mutations | Pederson and Setlow, 2001 |
| | | Mutations in divIVA locus | Cha et al., 1997 |
| | B.s. 168 | ts initiation mutation TsB143 | Sargent, 1975 |
| *Bacillus cereus* | WSBC 10030 | Induced by exposure to long-chain polyphosphate | Maier et al., 1999 |
| *Shigella flexneri* (2a) | MC-1 | | Gemski et al., 1980 |
| *S. dysenteriae* (1) | MC-V | | Gemski et al., 1980 |
| *Lactobacillus* spp. | | Variant minicell-producing strains isolated from grains | Pidoux et al., 1990 |
| *Neisseria gonorrhoeae* | | deletion or overexpression of min homologues | Ramirez-Arcos et al., 2001; Szeto et al., 2001 |
| *Escherichia coli* | | MinA mutations | Frazer et al., 1975; Cohen et al. 1976 |
| | | MinB mutations and deletions | Adler et al., 1967; Davie et al., 1984; Schaumberg et al.; 1983; Jaffe et al., 1988; Akerlund et al., 1992 |
| | CA8000 | cya, crp mutations | Kumar et al.; 1979 |
| | | MukA1 mutation | Hiraga et al., 1996 |
| | | MukE, mukF mutations | Yamanaka et al., 1996 |
| | | hns mutation | Kaidow et al., 1995 |
| | DS410 | | Heighway et al., 1989 |
| | | χ1972, χ 1776 and χ 2076 | Curtiss, 1980 |
| | P678-54 | Temperature-sensitive cell division mutations | Adler et al. 1967; Allen et al., 1972; Hollenberg et al., 1976 |
| | | Induced by overexpression of minB protein | De Boer et al., 1988 |
| | | Induced by overexpression of minE protein or derivatives | Pichoff et al., 1995 |
| | | Induced by overproduction of ftsZ gene | Ward et al., 1985 |
| | | Induced by overexpression of sdiA gene | Wang et al., 1991 |
| | | Induced by overexpression of min genes from *Neisseria gonorrhoeae* | Ramirez-Arcos et al., 2001; Szeto et al., 2001 |
| | | Induced by exposure to EGTA | Wachi et al., 1999 |
| *Legionella pneumophila* | | Induced by exposure to ampicillin | Elliot et al., 1985 |

Minicells are produced by several different eubacterial strains and mechanisms including the overexpression of endogenous or exogenous genes involved in cell division, chromosomal replication and partitioning, mutations in such genes, and exposure to various chemical and/or physical conditions. For example, *E. coli* cells that overexpress the gene product FtsZ, a protein involved in the regulation of cell division, form minicells. Minicells are also produced by *E. coli* cells having a mutation in one or more genes of the min locus, which is a group of genes that encode proteins that are involved in cell division.

Eubacterial cells that have been shown to produce minicells include *Escherichia, Shigella, Bacillus, Lactobacillus, Salmonella, Legionella* and *Campylobacter*. Bacterial minicell-producing species of particular interest are *E. coli, Salmonella* spp., and *Bacillus subtilis*. These organisms are particularly amenable to manipulation by a variety of molecular and genetic methods, with a variety of well-characterized expression systems, including many episomal and chromosomal expression systems, as well as other factors and elements useful in the present invention.

Because minicells lack the chromosomal DNA of the parent cell, RNA and protein production in the minicells is dependent on the protein production components that segregate into the minicell during formation. It has been alternatively reported that few molecules of endogenous RNA polymerase segregate into minicells and that many RNA polymerase molecules follow plasmids into minicells. Introduction of an exogenous RNA polymerase to minicell-producing cells enhances expression of episomal elements in minicells. Such enhanced expression may allow for the successful expression of proteins in minicells, wherein such proteins are expressed poorly or not at all in unmodified minicells. In order to maximize the amount of RNA transcription from episomal elements in minicells, minicell-producing cell lines that express an RNA polymerase specific for certain episomal expression elements may be used. An example of an *E. coli* strain of this type, designated MC-T7, was created and used as is described in the Examples. Those skilled in the art will be able to make and use equivalent strains based on the present disclosure and their knowledge of the art. Minicell construction is discussed in more detail in U.S. patent application Ser. No. 10/154,951, filed May 24, 2003, which is hereby incorporated by reference in its entirety.

Production of minicells and protein production therefrom may occur using a variety of approaches or combination thereof. In one approach, minicells are formed and purified. Expression elements contained in the minicells are then stimulated or induced to produce gene products encoded by the expression elements. In another approach, minicell-producing parent cells containing one or more expression elements are stimulated or induced to express a protein of interest. Minicell production is subsequently induced in this approach. In yet another approach, minicell production and protein production are co-induced. The disclosed methods of minicell production teach the exploitation of any timing variable of minicell formation or protein production to optimize minicell and protein production It is desirable to optimize minicell and protein production from minicell producing parent cells because these functions can be detrimental to the host cells. Using inducible minicell and protein production systems permits one to minimize the deleterious effects of these procedures. For example, an inducible promoter can be used to control the expression of one or more genes that induce minicell formation. The same inducible promoter or a different inducible promoter can be used to control protein expression from the minicells. Yields of immunogenic minicells can be optimized by timing the induction of minicell production from a minicell producing parent cell line with induction of protein production from one or more expression vectors encapsulated within the minicell.

Minicell Purification

A variety of methods are used to separate minicells from parent cells. In general, such methods are physical, biochemical and genetic, and can be used in combination. The objective of these methods is to minimize or eliminate parental cell contamination in the minicell compositions produced using the described methods. For example, minicells are separated from parent cells using glass-fiber filtration and centrifugation, both differential and zonal, size-exclusion chromatography, differential sonication, and freeze-thaw cycles.

One centrifugation technique provides for the purification of minicells can be purified using a double sucrose gradient. The first centrifugation involves differential centrifugation, which separates parent cells from minicells based on differences in size or density. The percent of sucrose in the gradient (graduated from about 5 to about 20%), Ficol or glycerol is designed to allow only parent cells to pass through the gradient.

The supernatant, which is enriched for minicells, is then separated from the pellet and is spun at a much higher rate (for example, $\geq 11,000 \times g$). This pellets the minicells and any parent cells that did not pellet out in the first spin. The pellet is then resuspended and layered on a sucrose gradient.

The band containing minicells is collected, pelleted by centrifugation, and loaded on another gradient. This procedure is repeated until the minicell preparation is essentially depleted of parent cells, or has a concentration of parent cells that is low enough so as to not interfere with a chosen minicell application or activity. A variety of buffers and media may be used during these purification procedures. These buffers are chosen for their ability to maintain the integrity of the minicells during the purification process. Buffers and media used in these procedures may serve as an osmo-protectant, stabilizing agent, or energy source, or may contain agents that limit the growth of contaminating parental cells.

Contaminating parental cells may be eliminated from minicell preparations by incubation under conditions that selectively kills dividing cells. Because minicells neither grow nor divide, they are resistant to such treatments. An example of conditions that prevent or kill dividing parental cells is treatment of a parent cell culture with an antibacterial agent, such as penicillin. Penicillin prevents cell wall formation and leads to lysis of dividing cells. Other agents may be used to prevent division of parental cells. Such agents include azide. Azide is a reversible inhibitor of electron transport, and thus prevents cell division. Additional examples of compounds capable of eliminating or inhibiting the division of parent cells include D-cycloserine and phage MS2 lysis protein. Khachatourians (U.S. Pat. No. 4,311,797) states that it may be desirable to incubate minicell/parent cell mixtures in brain heart infusion broth at 36° C. to 38° C. prior to the addition of penicillin G and further incubations.

Alternatively, lytic phage infection can be used to selectively kill, and preferably lyse, minicell producing parent cells. For example, although minicells can internally retain M13 phage in the plasmid stage of the M13 life cycle, they are refractory to infection and lysis by M13 phage. In contrast, minicell producing parent cells are infected and lysed by M13 and are thus are selectively removed from a mixture comprising parent cells and minicells. For example, a mixture comprising parent cells and minicells is treated with M13 phage at a multiplicity of infection (M.O.I.) of 5. The infection is allowed to continue to a point where $\geq 50\%$ of the parent cells are lysed, preferably $\geq 75\%$, more preferably $\geq 95\%$ most preferably $\geq 99\%$; and $\leq 25\%$ of the minicells are lysed or killed, preferably $\leq 15\%$, most preferably $\leq 1\%$.

Another example of a method by which minicell producing parent cells can be selectively killed, and preferably lysed, exploits the presence of a conditionally lethal gene present in a chromosome of the parent cell. Induction of the chromosomal lethal gene results in the destruction of parent cells, but does not impact minicells as they lack the chromosome harboring the conditionally lethal gene. For example, a parent cell may contain a chromosomal integrated bacteriophage comprising a conditionally lethal gene, such the temperature sensitive repressor gene lambda c1857. Induction of this phage, which results in the destruction of the parent cells but not of the achromosomal minicells, is achieved by simply raising the temperature of the growth media. A preferred bacteriophage to be used in this method is one that kills or lyses the parent cells but does not produce infective particles. Expression of a toxic protein or proteins can also be used to selectively kill or lyse minicell producing parental cells. For example, expression of a phage holing gene can be used to lyse parental cells to improve the purity of minicell preparations.

Modified Forms of Gram-negative Minicells

Gram-negative eubacterial cells and minicells are bounded by an inner membrane (IM), which is surrounded by a cell wall, wherein the cell wall is itself enclosed within an outer membrane (OM). In certain embodiments, it is desirable to use fully intact minicells to stimulate an immunogenic response. In different aspects of the invention, it is preferred to disrupt or degrade the outer membrane, cell wall or inner membrane of a eubacterial minicell. Such treatments can be used to increase or decrease the immunogenicity of a minicell.

Eubacterial cells and minicells with altered membranes and/or cell walls are called "poroplasts" "spheroplasts," and "protoplasts." Herein, the terms "spheroplast" and "protoplast" refer to spheroplasts and protoplasts prepared from minicells. In contrast, "cellular spheroplasts" and "cellular protoplasts" refer to spheroplasts and protoplasts prepared from cells. Also, as used herein, the term "minicell" encompasses not only minicells per se but also encompasses poroplasts, spheroplasts and protoplasts.

In a poroplast, the eubacterial outer membrane and lipopolysaccharide components have been removed. In a spheroplast, portions of a disrupted eubacterial outer membrane or disrupted cell wall may remain associated with the inner membrane of the minicell. The membrane and cell wall of the spheroplast is nonetheless porous because the permeability of the disrupted outer membrane and cell wall has been increased. A membrane is "disrupted" when the membrane's structure has been treated with an agent or incubated under conditions that lead to the partial degradation of the membrane, thereby increasing the permeability thereof. In contrast, a membrane that has been "degraded" is essentially, for the applicable intents and purposes, removed. In preferred embodiments, irrespective of the condition of the outer membrane and cell wall, the eubacterial inner membrane is not disrupted. Additionally, membrane proteins displayed on the inner membrane are accessible to compounds that are brought into contact with the minicell, poroplast, spheroplast, protoplast or cellular poroplast.

Poroplasts

For various applications poroplasted minicells are capable of preserving the cytoplasmic integrity of the minicell while producing increased stability over that of naked protoplasts. Maintenance of the cell wall in poroplasted minicells increases the osmotic resistance, mechanical resistance and storage capacity over protoplasts while permitting passage of small and medium size proteins and molecules through the porous cell wall.

A poroplast is a Gram-negative bacterium that has its outer membrane removed. The production of poroplasts involves a modification of the procedure to make protoplasts to remove the outer membrane. Like protoplasts, measuring the total lipopolysaccharide that remains in the poroplast preparation may be used to monitor the removal of the outer membrane. Endotoxin kits and antibodies reactive against lipopolysaccharide may be used to measure lipopolysaccharide in solution; increasing amounts of soluble lipopolysaccharide indicates decreased retention of lipopolysaccharide by protoplasts. This assay thus makes it possible to quantify the percent removal of total outer membrane from the poroplasted minicells.

Several chemical and physical techniques have been employed to remove the outer membrane of Gram-negative bacteria. Chemical techniques include the use of EDTA in Tris to make cells susceptible to hydrophobic agents such as actinomycin. Lactic acid permeabilizes Gram-negative bacteria by disrupting the outer membrane. Physical techniques for removing the outer membrane include the use of osmodifferentiation to facilitate the disruption of the outer membrane.

Spheroplasts

A spheroplast is a bacterial minicell that has a disrupted cell wall or a disrupted outer membrane. Unlike eubacterial minicells and poroplasts that have a cell wall and can thus retain their shape despite changes in osmotic conditions, the absence of an intact cell wall in spheroplasts means that these minicells do not have a rigid form.

Protoplasts

A protoplast is a bacterium that has its outer membrane and cell wall removed. The production of protoplasts typically involves the use of lysozyme and high salt buffers to remove the outer membrane and cell wall. Various commercially available lysozymes can be used in such protocols. Measuring the total lipopolysaccharide that remains in the protoplast preparation is used to monitor the removal of the outer membrane. Commercially available endotoxin kits assays can be used to measure lipopolysaccharide in solution; increasing amounts of soluble lipopolysaccharide indicates decreased retention of lipopolysaccharide by protoplasts. This assay thus makes it possible to quantify the percent removal of total outer membrane from the minicells.

For minicell applications that utilize bacterial-derived minicells, it may be necessary to remove the outer membrane of Gram-negative cells and/or the cell wall of any bacterial-derived minicell. For Gram-positive bacterial cells, removal of the cell wall may be easily accomplished using lysozyme. This enzyme degrades the cell wall allowing easy removal of now soluble cell wall components from the pelletable protoplasted minicells. In a more complex system, the cell wall and outer membrane of Gram-negative cells may be removed by combination treatment with EDTA and lysozyme using a step-wise approach in the presence of an osmoprotecting agent. Examples of osmoprotectants include sucrose and glycerol.

It has been found that the concentration of the osmoprotectant sucrose, the cell wall digesting enzyme lysozyme, and chelator EDTA can be optimized to increase the quality of the protoplasts produced. Separation of either prepared Gram-negative spheroplasts prepared in either fashion from removed remaining lipopolysaccharide may occur through exposure of the spheroplast mixture to an anti-LPS antibody. The anti-LPS antibody may be covalently or non-covalently attached to magnetic, agarose, sepharose, sepheracyl, polyacrylamide, and/or sephadex beads. Following incubation, lipopolysaccharide is removed from the mixture using a magnet or slow centrifugation resulting in a protoplast-enriched supernatant.

Monitoring loss of LPS may occur through dot-blot analysis of protoplast mixtures or various commercially available endotoxin kit assays can be used to measure LPS in solution; increasing amounts of soluble LPS indicates decreased retention of LPS by protoplasts. This immunoassay may comprise a step of comparing the signal to a standard curve in order to quantify the percent removal of total outer membrane from the minicells. Lipopolysaccharide removal has also been measured by gas chromatography of fatty acid methyl esters.

Minicells from L-form Eubacteria

L-form bacterial strains can be used to prepare antigenic minicells. L-form bacterial strains lack an outer membrane, a cell wall, a periplasmic space and extracellular proteases. Thus, in L-form Eubacteria, the cytoplasmic membrane is the only barrier between the cytoplasm and its surrounding environment.

Segregation of minicells from L-form eubacterial parent cells allows for the generation of minicells that are at least partially deficient in barriers that lie outside of the cytoplasmic membrane, thus providing direct access to components displayed on the minicell membrane. Thus, depending on the strains and methods of preparation used, minicells prepared from L-form eubacterial parent cells will be similar if not identical to various forms of poroplasts, spheroplasts and protoplasts. Displayed components that are accessible in L-form minicells include, but are not limited to, lipids, small molecules, proteins, sugars, nucleic acids and/or moieties that are covalently or non-covalently associated with the cytoplasmic membrane or any component thereof.

L-form Eubacteria that can be used in the methods of the invention include species of *Escherichia, Streptomyces, Proteus, Bacillus, Clostridium, Pseudomonas, Yersinia, Salmonella, Enterococcus* and *Erwinia*.

Assaying Minicells

Levels of minicell production can be evaluated using methods described herein. Relatively high levels of minicell production are generally preferred. Minicell production can be assessed by microscopic examination of late log-phase cultures. The ratio of minicells to normal cells and the frequency of cells actively producing minicells are parameters that increase with increasing minicell production.

Recombinant DNA Expression in Minicells

Recombinant expression of an antigen of interest typically requires the use of an expression element, such as an expression cassette or construct. The expression element contains an open reading frame encoding the antigen of interest that is introduced into an appropriate minicell producing parent cell to generate a minicell expression system. Expression elements of the invention may be introduced into a recipient eubacterial or eukaryotic minicell producing parent cell either as a DNA or RNA molecule, which may be a linear molecule or, more preferably, a closed covalent circular molecule. Expression from the expression element may occur through transient expression of the introduced sequence. Alternatively, permanent expression of the expression element may occur through the integration of the introduced expression cassette into the chromosome of the minicell producing parent cell.

A variety of recombinant expression systems can be used to produce the antigens for use with the disclosed invention. Any minicell producing parent cell that can be used to express an antigen of interest are suitable for use with the disclosed methods. Examples of recognized eubacterial hosts that may be used in the present invention include bacteria such as *E. coli, Bacillus, Streptomyces, Pseudomonas, Salmonella*, and *Serratia*.

Eubacterial expression systems utilize plasmid and viral expression vectors that contain replication sites and control sequences derived from a species compatible with the minicell producing parent cell line may be used. Suitable phage or bacteriophage vectors include λgt10 and λgt11. Suitable virus vectors may include pMAM-neo and pKRC. Appropriate eubacterial plasmid vectors include those capable of replication in *E. coli*, such as pBR322, pUC118, pUC119, ColEI, pSC101, and pACYC 184. *Bacillus* plasmids include pC194, pC221, and pT127. Suitable *Streptomyces* plasmids include p1J101 and *Streptomyces* bacteriophages such as C31. *Pseudomonas* plasmids are also known in the art.

To express an antigen in a eubacterial cell, typically one will operably link an open reading frame (ORF) encoding an antigen of interest to a functional promoter. Such promoters can be constitutive or more preferably, inducible. Examples of constitutive promoters include the int promoter of bacteriophage lambda, the bla promoter of the beta-lactamase gene sequence of pBR322, and the cat promoter of the chloramphenicol acetyl transferase gene sequence of pPR325. Examples of inducible eubacterial promoters include the major right and left promoters of bacteriophage lambda ($P_L$ and $P_R$), the trp, recA, lacZ, lad, and gal promoters of *E. coli*, the alpha-amylase and the sigma-28-specific promoters of *B. subtilis*, the promoters of the bacteriophages of *Bacillus*, and *Streptomyces* promoters.

Mammalian expression systems utilize host cells such as HeLa cells, cells of fibroblast origin such as VERO or CHO—K1, or cells of lymphoid origin and their derivatives. Preferred mammalian host cells include SP2/0 and J558L, as well as neuroblastoma cell lines such as IMR 332, which may provide better capacities for correct post-translational processing. Non-limiting examples of mammalian extrachromosomal expression vectors include pCR3.1 and pcDNA3.1, and derivatives thereof including those that are described by and are commercially available from INVITROGEN (Carlsbad, Calif.).

Several expression vectors are available for the expression of polypeptides in mammalian minicell producing parent cells. A wide variety of transcriptional and translational regulatory sequences may be employed, depending upon the nature of the minicell producing parent cell. The transcriptional and translational regulatory signals may be derived from viral sources, such as adenovirus, bovine papilloma virus, cytomegalovirus (CMV), simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals that are temperature-sensitive since, by varying the temperature, expression can be repressed or initiated, or are subject to chemical (such as metabolite) regulation.

Preferred eukaryotic plasmids include, for example, BPV, vaccinia, SV40, 2-micron circle, and the like, or their derivatives. Such plasmids are well known in the art (Botstein et al., Miami Wntr. Symp. 19:265-274, 1982; Broach, in: The Molecular Biology of the Yeast *Saccharomyces*: Life Cycle and Inheritance, Cold Spring Harbor Laboratory, Cold Spring Harbor, N.Y., p. 445-470, 1981; Broach, Cell 28:203-204, 1982; Bollon et al., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980).

Expression of polypeptides in eukaryotic hosts generally involves the use of eukaryotic regulatory regions. Such regions will, in general, include a promoter region sufficient to direct the initiation of RNA synthesis. Preferred eukaryotic promoters include, the promoter of the mouse metallothionein I gene, the TK promoter of Herpes virus, the SV40 early promoter, and the yeast gal4 gene sequence promoter.

Expression sequences and elements are also required for efficient expression. Examples of such sequences include Kozak and IRES elements in eukaryotes, and Shine-Delgarno sequences in prokaryotes, which direct the initiation of translation (Kozak, Initiation of translation in prokaryotes and eukaryotes. Gene, 1999. 234: 187-208; Martinez-Salas et al., Functional interactions in internal translation initiation directed by viral and cellular IRES elements, Jour. of Gen. Virol. 82:973-984, 2001); enhancer sequences; optional sites for repressor and inducers to bind; and recognition sites for enzymes that cleave DNA or RNA in a site-specific manner. Translation of mRNA is generally initiated at the codon, which encodes the first methionine residue; if so, it is preferable to ensure that the linkage between a eukaryotic promoter and a pre-selected open reading frame (ORF) does not contain any intervening codons that encode a methionine. The presence of such codons results either in the formation of a fusion protein with an uncharacterized N-terminal extension (if the AUG codon is in the same reading frame as the open reading frame) or a frame-shift mutation (if the AUG codon is not in the same reading frame as the open reading frame).

Expression of Antigenic Proteins

In a preferred embodiment, antigens of interest are expressed and presented on the surface of minicells. In one embodiment, antigens of interest are expressed as integral membrane proteins using a minicell producing expression system. The expressed antigens are displayed to a host immune system. Minicell producing cells or minicells harboring an expression vector are used to express the antigen of interest.

An "expression vector" is typically a nucleic acid encoding an open reading frame operably linked to one or more expression sequences that direct the expression of the open reading frame. The term "operably linked" means that the open reading frame is positioned with respect to expression sequences so that the amino acid sequence encoded by the open reading frame is faithfully transcribed, producing a gene product. The term "gene product" refers to either a nucleic acid (the product of transcription, reverse transcription, or replication) or a polypeptide (the product of translation) that is produced using the non-vector nucleic acid sequences as a template.

In one embodiment, it is preferable to use an expression construct that is an episomal expression construct. Minicells produced from a minicell producing cell line that has been transformed with an episomal expression construct will contain one or more of the expression constructs. These minicells are capable of expressing an open reading frame incorporated into the episomal expression construct. More specifically, these minicells will direct the production of the polypeptide encoded by the open reading frame using the RNA and ribosomal machinery that segregated into the minicell at the minicell budded off from the parent cell. At the same time, any mRNA molecules transcribed from a chromosomal gene prior to minicell formation that have been transferred to the minicell are degraded by endogenous RNases without being replaced by new transcription from the (absent) bacterial chromosome.

Chromosomal-encoded mRNAs will not be produced in minicells and will be "diluted" as increasing amounts of mRNAs transcribed from the episomal element are generated. A similar dilution effect is expected to increase the relative amount of episomally-generated proteins relative to any chromosome-encoded proteins present in the minicells. It is thus possible to generate minicells that are enriched for proteins encoded by and expressed from episomal expression constructs.

It is also possible to transform minicells with exogenous DNA after they have been prepared or separated from their parent cells. For example, phage RNA is produced in minicells after infection by lambda phage, even though replication of lambda phage may not occur in minicells.

Because it is the most characterized minicell-producing species, many of these episomal elements have been examined in minicells derived from *E. coli*. It is understood by practitioners of the art, however, that many episomal elements that are expressed in *E. coli* also function in other eubacterial species, and that episomal expression elements for minicell systems in other species are available for use in the invention disclosed herein.

Eukaryotic and archaebacterial minicells can also be used for expression of membrane proteins. Use of eukaryotic and archaebacterial minicells may be desirable when an antigen of interest expressed in such a minicell has enhanced or altered activity after they undergo post-translational modification processes such as phosphorylation, proteolysis, mystrilation, GPI anchoring and glycosylation.

Expression elements comprising expression sequence operably linked to open reading frames encoding the membrane proteins of interest are transformed into eukaryotic cells according to methods and using expression vectors known in the art. By way of non-limiting example, primary cultures of rat cardiomyocytes have been used to produce exogenous proteins after transfection of expression elements therefor by electroporation.

Yeast cells that produce minicells are transformed with expression elements comprising an open reading frame encoding a membrane protein operably linked to yeast expression sequences. Cells that harbor a transferred expression element may be selected using a gene that is part of the expression element that confers resistant to an antibiotic, such as neomycin.

Alternatively, in one aspect of the invention, bacterial minicells are prepared that contain expression elements that are prepared from shuttle vectors. A "shuttle vector" has sequences required for its replication and maintenance in cells from two different species of organisms, as well as expression elements, at least one of which is functional in bacterial cells, and at least one of which is functional in yeast cells. For example, *E. coli*-yeast shuttle vectors are known in the art and include those derived from Yip, Yrp, Ycp and Yep. Preferred *E. coli-yeast* shuttle vectors are episomal elements that can segregate into yeast minicells. Particularly preferred are expression vectors of the Yep (yeast episomal plasmid) class, and other derivatives of the naturally occurring yeast plasmid known as the 2 μm circle. The latter vectors have relatively high transformation frequencies and are stably maintained through mitosis and meiosis in high copy number.

Expression of antigens in eubacterial systems comprising an inner and outer membrane can have the expressed antigenic protein directed to either the outer membrane, the periplasmic space, the inner membrane, or the cytoplasm.

Detecting Protein Synthesis in Minicells

Methods for detecting and assaying protein production are known in the art. For example, transformed *E. coli* minicell-producing cells are grown in LB broth with the appropriate antibiotic overnight. The following day the overnight cultures are diluted 1:50 in fresh media, and grown at 37° C. to mid-log phase. If it is desired to eliminate whole cells, an antibiotic that kills growing (whole) cells but not quiescent cells (minicells) may be used. For example, in the case of cells that are not ampicillin resistant, ampicillin (100 mg per ml is added), and incubation is allowed to continue for about 2 more hours. Cultures are then centrifuged twice at low speed to pellet most of the large cells. Minicells are pelleted by spinning 10 minutes at 10,000 rpm, and are then resuspended in M63 minimal media supplemented with 0.5% casamino acids, and 0.5 mM cAMP, or M9 minimal medium supplemented with 1 mM $MgSO_4$, 0.1 mM $CaCl_2$, 0.05% NaCl, 0.2% glucose, and 1 ng per ml thiamine. Labeled ($^{35}$S) methionine is added to the minicells for about 15 to about 90 minutes, and minicells are immediately collected afterwards by centrifugation for 10 min at 4° C. and 14,000 rpm. Cells are resuspended in 50 to 100 μg Laemmeli-buffer, and disrupted by boiling and vortexing (2 minutes for each step). Incorporation of $^{35}$S-methionine was determined by measuring the amount of radioactivity contained in 1 μl of the lysate after precipitation of proteins with trichloroacetic acid (TCA). Minicell lysates (50,000 to 100,000 cpm per lane) are subjected to 10% PAGE. Gels are fixed and images there of are generated by autoradiography or any other suitable detection systems.

Minicell Modifications

A variety of compounds or moieties can be chemically attached (conjugated) to minicells via membrane proteins that are displayed on the minicells. The compound to be conjugated to minicells (the "attachable compound") may of any chemical composition, for example, small molecules, nucleic acids, radioisotopes, lipids or polypeptides.

It is possible to prepare minicells that express transmembrane proteins with cysteine moieties on extracellular domains. Linkage of the membrane protein may be achieved through surface cysteinyl groups by, for example, reduction with cysteinyl residues on other compounds to form disulfide bridges. If appropriate cysteinyl residues are not present on the membrane protein they may be introduced by genetic manipulation. To illustrate, bioactive lysosphingolipids (such as sphingosine, sphingosine-1-phosphate, and sphingosylphosphoryl choline) can be covalently linked to proteins expressed on the surfaces of minicells such that these bioactive lipids are on the surface of the minicells.

When the attachable moiety and the membrane protein both have a reduced sulfhydryl group, a homobifunctional cross-linker that contains maleimide, pyridyl disulfide, or beta-alpha-haloacetyl groups may be used for cross-linking. Examples of such cross-linking reagents include bismaleimidohexane (BMH) or 1,4-Di-[3'-(2'-pyridyldithio)propionamido]butane (DPDPB). Alternatively, a heterobifunctional cross-linker that contains a combination of maleimide, pyridyl disulfide, or beta-alpha-haloacetyl groups can be used for cross-linking.

Attachable moieties may also be chemically conjugated using primary amines. In these instances, a homobifunctional cross-linker that contains succiminide ester, imidoester, acylazide, or isocyanate groups may be used for cross-linking. Examples of such cross-linking reagents include, but are not limited to: Bis[2-(succinimidooxycarbonyloxy)ethyl]sulfone (BSOCOES); Bis[2-(sulfosuccinimidooxycarbonyloxy)ethyl]sulfone (sulfo-BSCOCOES); Disuccinimidyl suberate (DSS); Bis-(Sulfosuccinimidyl) Suberate (BS3); Disuccinimidyl glutarate (DSG); Dithiobis(succinimidylpropionate) (DSP); Dithiobois(sulfosuccinimidylpropionate) (DTSSP); Disulfosuccinimidyl tartrate (sulfo-DST); Dithio-bis-maleimidoethane (DTME); Disuccinimidyl tartrate (DST); Ethylene glycolbis(sulfosuccinimidylsuccinate) (sulfo-EGS); Dimethyl malonimidate.2HCl (DMM); Ethylene glycolbis (succinimidylsuccinate) (EGS); Dimethyl succinimidate.2HCl (DMSC); Dimethyl adipimidate.2HCl (DMA); Dimethyl pimelimidate.2HCl (DMP); and Dimethyl suberimidate.2.HCl (DMS), and Dimethyl 3,3'-dithiobispropionimidate.2HCl (DTBP). Heterobifunctional cross-linkers that contains a combination of imidoester or succinimide ester groups may also be used for cross-linking.

Attachable moieties may also be chemically conjugated using sulfhydryl and primary amine groups. In these instances, heterobifunctional cross-linking reagents are preferable used. Examples of such cross-linking reagents include, but are not limited to: N-succinimidyl 3-(2-pyridyldithio) propionate (DPDP); N-succinimidyl 6-[3'-(2-pyridyldithio)-propionamido]hexanoate (sulfo-LC-SPDP); m-maleimidobenzoyl-N-hydroxysuccinimide ester (MBS); m-maleimidobenzoyl-N-hydroxysulfosuccinimide ester (sulfo-MBS); succinimidyl 4-[P-maleimidophenyl]butyrate (SMPB); sulfosuccinimidyl 4-[p-maleimidophenyl]butyrate (sulfo-SMPB); N-[4-Maleimidobutyryloxy]succinimide ester (GMBS), N-[4-maleimidobutyryloxy]sulfosuccinimide ester (sulfo-GMBS); N-[4-maleimidocaproyloxy]succinimide ester (EMCS); N-[4-maleimidocaproyloxy]sulfosuccinimide ester (sulfo-EMCS); N-succinimidyl(4-iodoacetyl) aminobenzoate (STAB); sulfosuccinimidyl(4-iodoacetyl) aminobenzoate (sulfo-SLAB); succinimidyl 4-(N-maleimidomethyl)cyclohexane-1-carboxylate (SMCC); sulfosuccinimidyl 4-(N-maleimidomethyl)cyclohexane-1-carboxylate (sulfo-SMCC); succiminidyl-4-(N-maleimidomethyl)cyclohexane-1-carboxy-(6-amido-caproate) (LC-SMCC); 4-succinimidyloxycarbonyl-methyl-(2-pyridyldithio) toluene (SMPT); and sulfo-LC-SMPT.

As an exemplary protocol, a minicell suspension is made 5 mM EDTA/PBS, and a reducing solution of 2-mercaptoethylamine in 5 mM EDTA/PBS is added to the minicells. The mixture is incubated for 90 minutes at 37° C. The minicells are washed with EDTA/PBS to remove excess 2-mercaptoethylamine. The attachable moiety is dissolved in PBS, pH 7.2. A maleimide crosslinker is added to the solution, which is then incubated for 1 hour at room temperature. Excess maleimide is removed by column chromatography.

The minicells with reduced sulfhydryl groups are mixed with the derivatized compounds having an attachable moiety. The mixture is allowed to incubate at 4° C. for 2 hours or overnight to allow maximum coupling. The conjugated minicells are washed to remove unreacted (unattached) compounds having the attachable moiety. Similar protocols are used for expressed membrane proteins with other reactive groups (e.g., carboxyl, amine) that can be conjugated to an attachable moiety.

Minicell Delivery of DNA Encoding Protective Antigens

Presenting protective antigens to a subject can induce a prophylactic immune response. The prophylactic immune response is more effective if the protective antigens presented are in a native state. The more accurately the protective antigen represents the native antigen, the more authentic the immune response generated.

Minicells can be used to deliver plasmid DNA that encodes protective antigens from pathogens. Minicells that deliver DNA encoding protective antigens produce a more authentic immune response that is more similar to infection-induced immunity. One possible explanation for this result is that DNA immunization that transfects host cells with a plasmid that encodes and expresses one or more protective antigens provides antigens to the host's immune system that are in a native state.

Minicell-mediated DNA immunization is advantageous to other methods of introducing plasmid DNA to a cell, for example by direct intramuscular or intradermal inoculation, because the plasmid DNA is introduced into a greater number of target cells using minicells rather than direct introduction of the plasmid DNA that encodes protective antigens.

In one embodiment, minicells containing one or more plasmids that encode one or more antigens of interest are provided to a subject. In one preferred embodiment, the plasmid encodes one or more heterologous antigens of interest. In another preferred embodiment, the minicells prepared with the antigen encoding plasmid are designed with one or more ligands on their surface that targets the minicells to a particular cell type. For example, a plasmid carrying minicell may express a cytokine or other ligand specific for a receptor on the target cell. A population of minicells displaying such a ligand would be targeted to the target cell designated. Once contacting a target cell, the minicell can then fuse with the target cell and introduce the plasmid DNA contained therein into the target cell. The control sequences within the plasmid DNA would then direct the synthesis of the antigen of interest from the plasmid DNA.

DNA immunization is superior to immunization by purified antigens because it induces a more balanced cellular and humoral immune response from a host. Antigens produced by a host cell are presented in the context of class I MHC antigens. This presentation of antigens has been shown to induce $T_H$ cells and CTLs. Accordingly, DNA immunization should be more likely to induce a cellular and humoral immune response from an immunized host than merely immunizing with a purified antigen alone. Additionally, foreign antigen introduced into a host by DNA immunization can be expressed in vivo for several months. Transfected cells present antigens over a longer period of time than live-attenuated or nonliving virus vaccines. The increased period of antigen presentation results in the generation of durable B- and T-cell responses.

While DNA immunization has its advantages, the technique has certain disadvantages. For example, the rate at which DNA immunization generates an immune response, has been reported to be slower than that generated by the administration of purified antigens. Minicell based DNA immunization can overcome this deficiency because minicells can both deliver the DNA encoding an immunogen and display one or more preformed purified antigen on the surface of the minicell. While the DNA vector can encode a different antigen from that which is displayed on the outer surface of the minicell, in a preferred embodiment, the DNA encodes the same antigen as is displayed.

One preferred embodiment of the invention relates to minicells that express at least one surface antigen and contain a plasmid designed to facilitate DNA immunization. Presenting preformed antigens and utilizing DNA immunization can be advantageous over DNA immunization alone because it provides an immediate supply of protective antigens to the host's immune system as well as a long term supply of antigens.

In a preferred embodiment a population of minicells is prepared that expresses protective antigens on the membrane of the minicell and carrying a plasmid within the minicell that encodes one or more protective antigens. In preferred embodiments, the plasmid encodes one or more antigens that are presented on the membrane of the minicell. A strong promoter encoded by the plasmid, that is active in a variety of mammalian cell types, typically drives expression of the protective antigen. An example of a promoter that can be used with a eukaryotic expression sequence is a Cytomegalovirus (CMV) promoter. In further embodiments, both eukaryotic and prokaryotic expression control sequences can be present on the plasmid.

Any of the eukaryotic promoters discussed above can be used to prepare a plasmid capable of directing protein expression in a host cells. Plasmid vectors encoding antigens based on the alphavirus replicon system and under control of the alphavirus subgenomic promoter have been reported.

In certain embodiments, a subject is provided a preparation of minicells that present protective antigens on their surfaces. These minicells also contain a DNA plasmid that encodes a protective antigen. It is believed that once these minicells are introduced into the subject, a certain percentage of the minicells are consumed by macrophages. The proteins of the minicell are processed into antigens and displayed to the host's immune system. The host mounts an antibody response against the antigens of the minicell. A portion of the remaining minicells bind to targeted immune cells and fuse with those target cells. The plasmid DNA contained within these minicells is introduced into the host target cell after the lipid bilayers of the target cell and the minicell fuse. By providing both preformed antigens and antigens encoded by DNA, this embodiment of the invention provides a short-term impetus to generate a humoral immune response and a long term impetus to generate both a humoral and cellular immune response.

Antigens presented to a host by immunization with DNA can encode any pathogenic open reading frame from any pathogen or source. For example, viral antigens, including antigens that can form virus-like particles, can be used to generate immunogenic compositions with activity agent the pathogen of interest. In addition, DNA encoding bacterial antigens and antigens characteristic of cancerous cells can also be used with the minicells described herein.

Formulation and Administration of Immunogenic Minicells

Formulations of immunogenic minicells include a suitable carrier. Because minicells may be destroyed by digestion or prevented from acting due to antibody secretion in the gut, they are preferably administered parenterally, including, for example, administration that is subcutaneous, intramuscular, intravenous, intradermal, nasal, mucosal, or via suppository. Formulations suitable for parenteral administration include aqueous and non-aqueous sterile injection solutions that may contain buffers, and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use.

The immunogenic formulations disclosed herein may include adjuvant systems for enhancing the immunogenicity of the formulation. Adjuvants are substances that can be used to augment or modulate an immune response. Typically an adjuvant and an antigen of interest are mixed prior to presentation to the immune system. Alternatively, the adjuvant and the antigen are presented separately. Examples of materials suitable for use in vaccine compositions are provided in Osol, A., ed., Remington's Pharmaceutical Sciences, Mack Publishing Co, Easton, Pa. (1980), pp. 1324-1341, which reference is entirely incorporated herein by reference.

Compositions comprising immunogenic minicells are injected into a human or animal at a dosage of about 0.1-1000 µg per kg body weight. Antibody titers against antigens of interest are determined by ELISA, using the recombinant protein and horseradish peroxidase-conjugated goat anti-human or animal immunoglobulins or other serologic techniques. Cellular immune responses to immunogenic minicells can also be measured using various assays well known to those of ordinary skill in the art. Booster injections are administered as needed to achieve the desired levels of protective antibodies or T cells.

Routes and frequency of administration, as well as the dosage of immunogenic minicell preparations will vary from individual to individual. Between 1 and 10 doses may be administered for a 52-week period. Preferably, 6 doses are administered, at intervals of 1 month, and booster administrations may be given periodically thereafter. Alternate protocols may be appropriate for individual patients.

Immunotherapy of hyperproliferative disorders using immunogenic minicell preparations typically comprises providing a suitable dose of minicells to a subject in need thereof. Efficacy of such a treatment can be monitored, as described above, by determining the degree an anti-tumor immune response results in response to the administration of the immunogenic minicells. The immune response of an immunized subject can be monitored by measuring the anti-tumor antibodies in a patient or by immunogen-dependent generation of cytolytic effector cells capable of killing the patient's tumor cells in vitro. Typically, an effective dose of a particular immunogenic minicell composition is capable of causing an immune response that leads to an improved clinical outcome in immunized subjects as compared to non-immunized subjects.

The immunogenic compositions according to the invention may contain a single or multiple species of immunogenic minicells where each species displays a different immunogen. Additionally or alternatively, immunogenic minicells may each display or express one or more immunogen.

Pharmaceutical Compositions

Another aspect of the invention is drawn to compositions, including pharmaceutical compositions. A "composition" refers to a mixture comprising at least one carrier, preferably a physiologically acceptable carrier, and one or more immunogenic minicell compositions. The term "carrier" defines a chemical compound that does not inhibit or prevent the incorporation of the immunologically active peptide(s) into cells or tissues. A carrier typically is an inert substance that allows an active ingredient to be formulated or compounded into a suitable form. Exemplary forms include a pill, a capsule, a gel, a film, a tablet, a microparticle, a solution, an ointment, a paste, an aerosol, a droplet, a colloid or an emulsion etc.

A "physiologically acceptable carrier" is a carrier suitable for use under physiological conditions that does not abrogate (reduce, inhibit, or prevent) the immunological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically acceptable carrier, in which the immunogenic minicell composition is disposed.

A "pharmaceutical composition" refers to a composition wherein the carrier is suitable for use in humans or other animals. The term "pharmaceutically acceptable carrier" includes any medium or material that is not biologically or otherwise undesirable. The carrier may be administered to an organism along with an immunogenic minicell composition without causing undesirable effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application.

The terms "therapeutically effective amount" or "pharmaceutically effective amount" mean an amount sufficient to induce or effectuate a measurable immunogenic response in the target cell, tissue, or body of an organism. What constitutes a therapeutically effective amount will depend on a variety of factors, which the knowledgeable practitioner will take into account in arriving at the desired dosage regimen.

The compositions of the invention can further comprise other chemical components, such as diluents and excipients. A "diluent" is a chemical compound diluted in a solvent, preferably an aqueous solvent, that facilitates dissolution of the composition in the solvent, and it may also serve to stabilize the immunogenic composition or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the activity of an immunologically active peptide.

An "excipient" is any more or less inert substance that can be added to a composition to confer a suitable property thereto. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See WO 98/52547 (which describes microsphere formulations for targeting compounds to the stomach, the formulations comprising an inner core (optionally including a gelled hydrocolloid) containing one or more active ingredients, a membrane comprised of a water insoluble polymer, such as ethylcellulose, to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The immunogenic minicell compositions of the invention can be formulated in any manner suitable for administration. Immunogenic minicell compositions may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition according to the invention is compressed into tablet or pill form suitable for oral administration or compounded into a sustained release formulation.

When the composition is intended for oral administration but is to be delivered to epithelium in the intestines, it is preferred that the formulation be encapsulated with an enteric coating to protect the formulation and prevent premature release of the immunogenic minicell compositions included therein. As those in the art will appreciate, the compositions of the invention can be placed into any suitable dosage form. Pills and tablets represent some of such dosage forms.

The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

In certain preferred embodiments the immunogenic compositions that comprise a bioadhesive, preferably a mucoadhesive, coating. A "bioadhesive coating" is a coating that allows a substance (e.g., a minicell composition) to adhere to a biological surface or substance better than occurs absent the coating. A "mucoadhesive coating" is a preferred bioadhesive coating that allows a substance, for example, a composition according to the invention, to adhere better to mucosa occurs absent the coating. For example, micronized particles having a mean diameter of about 5, 10, 25, 50, or 100 μm can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

The immunogenic minicell compositions of the invention may be administered to any organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (enema or suppository), aerosol (nasal or pulmonary delivery), parenteral, and topical administration.

Preferably, sufficient quantities of the immunogenic minicell composition are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the immunogenic minicell compositions of the invention are administered as agents to achieve a particular desired immunological result. The desired immunological result may include a therapeutic or protective effect. Suitable formulations and methods of administration of therapeutic agents include those for oral, pulmonary, nasal, buccal, ocular, dermal, rectal, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, micelle, liposome, and the like, incorporated into a pill, capsule, tablet, suppository, aerosol, droplet, or spray. Pills, tablets, suppositories, aerosols, powders, droplets, and sprays may have complex, multilayer structures and have a large range of sizes. Aerosols, powders, droplets, and sprays may range from small (1 micron) to large (200 micron) in size.

Pharmaceutical compositions of the present invention can be used in the form of a solid, a lyophilized powder, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0.1% or greater (See, e.g., U.S. Pat. No. 5,314,695, which is hereby incorporated in its entirety). The active compound is included in the pharmaceutical composition in an amount sufficient to produce the desired effect upon the process or condition of diseases.

Antigens From Category A Pathogens

Any antigen, including pathogenic and cancer antigens, can be used with the immunogenic minicells described herein. For example, pathogens from the NIAID Category A pathogen list can be used herein, and are discussed in detail below. A brief description of the NIAID Category A pathogen is provided along with a list of potential antigenic targets and accession numbers encoding those targets.

*Bacillus anthracis* (anthrax)

Anthrax is caused by *B. anthracis*. This organism is an extracellular toxinogenic bacterium. An anthrax vaccine comprising minicells that express spore antigens as well as antigens from the anthrax toxins is disclosed.

Spore Surface

The exosporium is the most external structure of the spore form of *B. anthracis*. A glycoprotein termed BclA (for *Bacillus* collagen-like) constituent of the exosporium has been identified. It contains a central region presenting similarity to mammalian collagen proteins. BclA is the structural component of the filaments located at the surface of the exosporium.

Toxins of *Bacillus anthracis*

*Bacillus anthracis* secretes two toxins composed of three proteins. The first toxin is the lethal toxin, which is composes of a protective antigen (PA) and a lethal factor (LF). The second toxin is the edema toxin, which is composed a PA and an edema factor (EF). The PA (protective antigen) is the common component able to bind and deliver EF (edema factor) and LF (lethal factor) into target eukaryotic cells. EF is a calmodulin-dependent adenylate cyclase and LF is a metalloprotease.

Forms of *Bacillus anthracis*

The vegetative form of the bacilli is encapsulated. The capsule covers a structural array termed S-layer. The S-layer is composed of two abundant proteins, Sap and EA1. The capsule is composed of at least three proteins, which genes belong to an operon, are necessary for capsule synthesis. There is a fourth protein encoded by the same operon that regulates capsule levels by degrading excess capsule protein.

Provided below is a table of various genes of *Bacillus anthracis* that can be expressed by minicells to generate immunogenic compositions. Note that this list of genes and their encoded proteins is not intended to be an exclusive list; rather, other genes and proteins from these and other species can be used.

|  | Protein | Strain | Accession Numbers |
|---|---|---|---|
| *Bacillus anthracis* | Bc1A genes | ATCC4229 | AJ516947 |
|  |  | CIP5725 | AJ516946 |
|  |  | RA3 | AJ516945 |
|  |  | 7611 | AJ516944 |
|  |  | ATCC6602 | AJ516943 |
|  |  | 6183 | AJ516942 |
|  |  | 9602 | AJ516941 |
|  |  | CIPA2 | AJ516940 |
|  |  | CIP53169 | AJ516939 |
|  |  | CIP8189 | AJ516938 |
|  |  | CIP7702 | AJ516937 |
|  |  | Ames | AJ516936 |
|  | PA genes | virulence plasmid pX01 | NC_001496 |
|  |  | A2012 plasmid pXO1 | NC_003980 |
|  |  | BA1024 | AF306783 |
|  |  | plasmid pX01 | AF306782 |
|  |  | isolate 33 | AF306781 |
|  |  | isolate BA1035 | AF306780 |
|  |  | isolate 28 | AF306779 |
|  | EF genes | virulence plasmid pX01 | NC_001496 |
|  |  | isolate IT-Carb3-6249 | AJ413931 |
|  |  | isolate IT-Carb1-6225 | AJ413930 |
|  |  | isolate Sterne | M24074 |
|  |  | isolate Sterne | M23179 |
|  | LF genes | virulence plasmid pX01 | NC_001496 |
|  |  | A2012 plasmid pXO1 | NC_003980 |
|  |  | clone: pLF74 | M29081 |
|  |  | virulence plasmid pX01 | M30210 |
|  | SAP genes | isolate Sterne | Z36946 |
|  | EA1 genes | isolate Sterne | X99724 |
|  | Capsule genes | A2012 plasmid pXO2, CapA, B, & C | NC_003981 |
|  |  | plasmid pX02 capR | AB017611 |

*Clostridium botulinum* (Botulism)

*Clostridium botulinum* is an anaerobic, rod-shaped spore producing bacterium that produces a protein with characteristic neurotoxicity. Antigenic types of *C. botulinum* are identified by complete neutralization of their toxins by the homologous antitoxin; cross-neutralization by heterologous antitoxins does not occur or is minimal. There are seven recognized antigenic types: A, B, C, D, E, F, and G. Types C and D are not thought to cause human disease, however this has not been definitively established.

Cultures of five of these types apparently produce only one type of toxin but all are given type designations corresponding to their toxin production. Types C and D cross-react with antitoxins to each other because they each produce more than one toxin and have at least one common toxin component. Type C produces predominantly $C_1$ toxin with lesser amounts of D and $C_2$, or only $C_2$, and type D produces predominantly type D toxin along with smaller amounts of $C_1$ and $C_2$. Mixed toxin production by a single strain of *C. botulinum* may be more common than previously realized. There is a slight reciprocal cross-neutralization with types E and F, and recently a strain of *C. botulinum* was shown to produce a mixture of predominantly type A toxin, with a small amount of type F.

*C. botulinum* is widely distributed in soils and in sediments of oceans and lakes. The finding of type E in aquatic environments by many investigators correlates with cases of type E botulism that were traced to contaminated fish or other seafood. Types A and B are most commonly encountered in foods subjected to soil contamination. In the United States, home-canned vegetables are most commonly contaminated with types A and B, but in Europe, meat products have also been important vehicles of foodborne illness caused by these types.

Provided below is a table of various genes of *C. botulinum* that can be expressed by minicells to generate immunogenic compositions.

|  | Protein | Strain | Accession Numbers |
|---|---|---|---|
| *Clostridium botulinum* | Neurotoxin Type A | 5' end | M27892 |
|  |  | isolate Kumgo, light chain-partial cds | AY166872 |
|  |  | Synthetic construct | AF464912 |
|  | Neurotoxin Type B | Isolate 1436 | AF295926 |
|  |  | isolate 13280 | AF300469 |
|  |  | isolate 667 | AF300468 |
|  |  | isolate 519 | AF300467 |
|  |  | isolate 593 | AF300466 |
|  |  | isolate 588 | AF300465 |
|  | Neurotoxin Type C | Isolate 6813 | D49440 |
|  |  | Botulinum bacteriophage | X62389 |
|  |  | Bacteriophage c-st | D90210 |
|  |  | C2 toxin component-I and component-II | D88982 |
|  |  | C2 toxin (component-I) | D63903 |
|  | Neurotoxin Type D | BVD/-3 | X54254 |
|  | Neurotoxin Type E | Isolate 35396 | AB082519 |
|  |  | Hazen 36208 | X70815 |
|  |  | VH Dolman | X70818 |
|  |  | NCTC 11219 | X62683 |
|  |  | Beluga | X62089 |
|  | Neurotoxin Type F | 202F | Y10770 |
|  |  | proteolytic F Langeland | X70821 |
|  |  | non-proteolytic Hobbs FT10 | X70820 |
|  |  | non-proteolytic Craig 610 | X70816 |
|  |  | 202F | M92906 |
|  | Neurotoxin Type G | synthetic sequence based on Wild type | AX608812 |
|  |  | 113/30, NCFB 3012 | X74162 |

*Yersinia pestis*

*Yersinia pestis* is the causative agent of plague. The nucleotide sequence of the organism's genome has been elucidated. "Genome sequence of *Yersinia pestis*, the causative agent of plague," Nature 413 523-527.

*Y. pestis* has been extensively studied and this work provides a number of potential targets for a subunit vaccine. Prime candidates include the F1 antigen (cfa1), pla, the V antigen (LcrV), and Yops. The YscC protein has been advanced identified as residing in the outer member of the organism and as such could also provide a potential vaccine target. See Clin Microbiol Rev. 10(1):35-66 (1997) for a more complete review.

Provided below is a table of various genes of *Y. pestis* that can be expressed by minicells to generate immunogenic compositions.

| | Protein | Strain | Accession Numbers |
|---|---|---|---|
| *Yersinia pestis* | Complete Genome | CO92 | NC_003143 |
| | | KIM | NC_004088 |
| | F1 Antigen (caf1) | caf1, caf1M, caf1A and caf1R | X61996 |
| | pla gene | KIM | AF053945 |
| | V antigen | CO-92 Biovar Orientalis | NC_003131 |
| | | Angola | AF167310 |
| | | Pestoides | AF167309 |
| | Yops | CO-92 Biovar Orientalis | NC_003131 |
| | | KIM5 | AF074612 |
| | | KIM | AF053946 |

Variola Major (Smallpox) and Other Pox Viruses

The smallpox virus genome has been completely sequenced.

| Organism | Protein | Strain | Accession Numbers |
|---|---|---|---|
| Variola major (smallpox) | Genome sequence | India-1967, ssp. major | NC_001611 |
| | | strain Bangladesh-1975 | L22579 |
| Vaccinia Virus | Genome Sequences | Ankara | U94848 |
| | Other Sequences | genomic DNA, 42 kbp | D11079 |
| | | Various genes | D00382 |
| | | Various genes | M36339 |
| | | Various genes | AF411106 |
| | | Various genes | AF411105 |
| | | Various genes | AF411104 |
| | | a13L ortholog gene for p8 | AJ309902 |
| | | | AJ315004 |
| | | A36R gene for p43-50 protein | AF120160 |
| | | DNA glycosylase (D4R and D5R) genes | L24385 |
| | | Various genes | M57977 |
| | | A33R (A33R) gene | AF226618 |
| | | L1R (L1R) gene | AF226617 |
| | | serine proteinase inhibitor | D00582 |

*Francisella tularensis* (tularemia)

*Francisella tularensis* is a small gram-negative coccobacillus. There are two main serotypes: Jellison Types A and B. Type A is considered the more virulent form. *F. tularensis* may be aerosolized in dry or wet form.

Viral Hemorrhagic Fevers

Arenaviruses

Arenavirues are enveloped. The surface of the virion envelope is studded with glycoprotein projections that consist of tetrameric complexes of the viral glycoproteins GP1 and GP2. Obtaining gene and amino acid sequences for these proteins from each of the arenaviruses listed below would be helpful in supporting a vaccine patent application.

LCM

Lymphocytic chorio meningitis (LCM) is caused by the lymphocytic chorio meningitis virus (LCMV). Studies in mice have shown that passive immunity is effective in protecting suckling mice from LCMV challenge. Because a protective immune response has been demonstrated, it may be possible to use minicell technology to produce large amounts of antibodies to treat victims of LCMV. Of course, a vaccine effective against LCMV would be a primary goal. LCMV appears to interact with CD+8 cells as part of its life cycle. The viral protein or proteins involved in this interaction would make prime targets for vaccine antigens using the disclosed minicell technology.

| Organism | Protein | Strain | Accession Numbers |
|---|---|---|---|
| LCMV | GP1 | WE | AJ233161 |
| | | Docile | AJ249159 |
| | | Docile | AJ249158 |
| | GP-C | CHV2 | U10158 |
| | | CHV3 | U10159 |
| | | CHV1 | U10157 |

Junin Virus

The Junin virus is a member of Arenaviridae. It is pleomorphic, enveloped globular virions 110-130 nm in diameter, linear, single-stranded, two-segmented RNA. Junin virus found mainly in Argentina and causes Argentinean hemorrhagic fever. Potential antigenic targets from the Junin virus include the GP1 and GP2 envelope glycoproteins. The NP, L and Z proteins are thought to be internal to the viral particle and would seem to be less likely targets. Nevertheless, these proteins can also be used to generate immunogenic compositions.

| Organism | Protein | Strain | Accession Numbers |
|---|---|---|---|
| Junin Virus | G1 (Partial) | PH3190 | AF264235 |
| | | PH7994 | AF264234 |
| | | PAn14823 | AF264233 |
| | | PH2412 | AF264232 |
| | GP-C | MC2 | D10072 |
| | NP | Vaccine Strain | U70804 |
| | Segment L | N/A | N/A |
| | Z | N/A | N/A |

Other arenavirues of interest include the Machupo virus, the Guanarito virus and the Lassa Fever genomic information and accession numbers for antigens of interest are provided below.

| Organism | Protein | Strain | Accession Numbers |
|---|---|---|---|
| Machupo Viruso | S Segment (Glycoprotein) | Carvallo | AY129248 |
| | | Carvallo | AF485260 |
| | nucleocapsid protein | AA288-77 | X62616 |
| Gaunarito | S Segment (Glycoprotein) | INH-95551 | AY129247 |
| | | INH-95551 | AF485258 |
| | nucleocapsid protein (Partial) | VHF-5603 | AF204207 |
| | | VHF-1150 | AF204206 |
| | | S-16995 | AF204205 |
| | | VHF-3990 | AF204204 |
| Lassa Virus | GP1 | 803213 | AF181854 |
| | | LP | AF181853 |
| | | 11620 | M15076 |
| | Segment L | Josiah | NC_004297 |
| | Segment S | Josiah | NC_004296 |
| | GP-C | AV | AF246121 |
| | Nucleoprotein | 11620 | J04324 |
| | | 803213 | AF181854 |
| | | LP | AF181853 |

Bunyaviruses:

Bunyaviruses are spherical particles that display surface glycoprotein projections of 5 to 10 nm, which are embedded in a lipid bilayered envelope approximately 5 to 7 nm thick. Depending on the virus, there can be from 270 to 1,400 glycoprotein spikes per virion. The spikes are generally thought to consist of heterodimers of the viral glycoproteins G1 and G2. The G1 and G2 proteins are decorated with N-linked carbohydrates, so this may make these viruses less attractive as targets. Two bunyaviruses of interest are the hantavirus and the Rift Valley fever virus. Sequence information for these viruses is provided below.

| Organism | Protein | Strain | Accession Numbers |
|---|---|---|---|
| Hantavirus | G1 & G2 | cl-1 | D25529 |
| | | 84FLi | AF366569 |
| | | B-1 | X53861 |
| | M Polypeptide | 84FLi | AF345636 |
| | | MF-43 | AJ011648 |
| | | 84FLi | AF366569 |
| | | Ls136V | AJ011647 |
| Rift Valley Fever Virus | Complete genome | ZH-548M12 | NC_002044 |
| | G1 & G2 | Rift Valley Fever Virus | M11157 |

Flaviviruses

There are a number of members of flavividae that are particularly attractive to serve as targets for a minicell immunogenic composition. Examples of pathogenic flaviviruses include the hepatitis C virus, St. Louis encephalitis virus, dengue, and a number of other encephalitis viruses. Sequence information for these viruses is provided below.

| Organism | Protein | Strain | Accession Numbers |
|---|---|---|---|
| Hepatitis C | Complete genome | M1LE | AB080299 |
| | | H77 | NC_004102 |
| | E protein | JB2-8 | AJ511254 |
| | | JB28-1 | AJ511253 |
| | | JB15-10 | AJ511252 |
| | M protein | N/A | N/A |
| | C protein | Gabonese | S73403 |
| | | Gabonese | S73404 |
| | | Gabonese | S73421 |
| St Louis encephalitis | E protein (partial) | BFS508 | AF112392 |
| | | FL79-411 | AF112391 |
| | | Hubbard | AF112389 |
| | M protein | N/A | N/A |
| | C protein | N/A | N/A |
| Dengue | Complete genome | 814669 | AF326573 |
| | | rDEN4del30 | AF326827 |
| | | 2Adel30 | AF326826 |
| | | N/A | NC_001474 |

Filoviruses

Filoviruses are enveloped viruses that can cause hemorrhagic fevers. Exemplary filoviruses include the Ebola and Marburg viruses. There are four species of Ebola-like viruses: Zaire, Sudan, Reston, and Côte d'Ivoire. There is only one representative of the Marburg filovirus. Each of these viruses contains VP40, GP, and VP24 proteins that are thought to be membrane-associated proteins. These proteins are candidates for vaccine targets using the disclosed minicell technology.

| Organism | Protein | Strain | Accession Numbers |
|---|---|---|---|
| Zaire Ebola virus | Complete genome | Mayinga | NC_002549 |
| | | Mayinga | AY142960 |

-continued

| Organism | Protein | Strain | Accession Numbers |
|---|---|---|---|
| Sudan Ebola virus | NP | Boniface | AF173836 |
| | SP | Boniface | U28134 |
| | L | Maleo 1979 | U23458 |
| | GP | Maleo | U23069 |
| Reston Ebola virus | Complete genome | Pennsylvania | NC_004161 |
| | | Reston | AB050936 |
| Cote d'Ivoire Ebola virus | Complete genome | N/A | N/A |
| Marburg virus | Complete genome | Popp | NC_001608 |
| | NP, VP35, VP40, GP, VP30, VP24, L genes | Popp | Z29337 |
| | | Musoke | Z12132 |

EXAMPLES

Example 1

Construction of an Inner Membrane Expression Vector pMPX200

The pMPX-200 expression vector was designed to express a gene product of interest as an inner membrane-bound, periplasmic exposed fusion protein. The nucleotide sequence of this vector is provided as SEQ ID NO: 1 and is shown without a coding sequence of interest. To construct an expression vector containing a coding sequence of interest, one inserts the gene or coding sequence of interest into the SalI/XbaI restriction region of the pMPX200 expression vector to create a chimeric fusion with the transmembrane domain (TMD) of toxR.

Example 2

Construction of an Outer Membrane Expression Vector pMPX201

The pMPX-201 expression vector was designed to express a gene product of interest as an outer membrane-bound, extracellular exposed fusion protein. The nucleotide sequence of this vector is provided as SEQ ID NO: 2 and is shown without a coding sequence of interest. To construct an expression vector containing a coding sequence of interest, one inserts the gene or coding sequence of interest into the XhoI/XbaI restriction region of the pMPX201 expression vector to create a chimeric insertion into lamB.

Example 3

ToxR-*Bacillus anthracis* PA Fusion Protein

Immunogenic minicells expressing the soluble *Bacillus anthracis* protective antigen (PA) on the outer membrane of an *E. coli* derived minicell are prepared and purified according to the protocols discussed in Examples 1 and 3. *E. coli* derived minicells transformed with the expression vector discussed in Example 1 but lacking the ToxR::PA fusion protein coding sequence are also prepared as a negative control. The two species of minicells are then formulated for intramuscular injection.

Minicells displaying the ToxR::PA fusion protein are provided to a group of test subjects. On day 1 the test subjects are provided with an initial dose of an inoculum comprising the ToxR::PA fusion protein expressing minicells. Control subjects are provided with an initial dose of an inoculum comprising minicells that do not express the ToxR::PA fusion protein. A booster is provided to each group of animals approximately two weeks later. Approximately 14 days after the initial immunization, blood is taken from the test and control subjects and used in an ELISA to determine if the subjects have mounted an antibody response against the inoculum. Serum analyzed by ELISA indicates that the test subjects mount an antibody response against the fusion protein inoculum. Serum taken from the control animals indicates that while the animals mounted an antibody response against the minicells themselves, they have not produced antibodies that react with the ToxR::PA fusion protein.

Lymphocytes isolated from the test groups of animals are shown to be reactive with the fusion protein expressing minicells. Lymphocytes isolated from the control group animals are shown not to be reactive with the fusion protein expressing minicells.

Approximately three weeks after the initial inoculation, the test animals are challenged with live *Bacillus anthracis*. The test subjects are completely protected from the development of anthrax symptoms while the control subjects die from anthrax.

Example 4

Minicell-Based DNA Delivery of GFP-Encoding Plasmids in a Mouse

Introduction

The purpose of this study was to demonstrate the capability of bacterial minicells to deliver plasmid DNA to cells in vivo for expression of a target protein. For the purpose of these experiments, nucleic acid encoding Green Fluorescent Protein (GFP) was used as the target protein. The read out for these experiments was the production of antibodies against GFP. The theory of the experiment is that if GFP were expressed by cells in a live mouse, the mouse's immune system would mount an immune response against the produced GFP, resulting in an antibody response. Without successful delivery of the plasmid DNA by the minicell and the subsequent expression by the mouse cell, an antibody response would not be obtained.

Methods

Three general types of minicells were created. Each of the three types of minicells contained a plasmid having nucleic acid encoding Green Fluorescent Protein (GFP). The first type of minicell included a plasmid containing a eubacterial expression sequence operably linked to the GFP nucleic acid, and did not contain a eukaryotic expression sequence. This plasmid was therefore designed to produce GFP protein in the minicell and not the animal target (administered to Group No. 4). The second type of minicell included a plasmid containing a eukaryotic expression sequence (CMV promoter) operably linked to the GFP nucleic acid, as opposed to a eubacterial expression sequence. This expression cassette was designed to drive the in vivo expression of the GFP protein in the cells within the target mouse (administered to Group No. 5). The third type of minicell included a plasmid having both eubacterial and eukaryotic expression sequences operably linked to the GFP nucleic acid. This third expression cassette was designed to drive expression of GFP in the minicell and the in vivo expression of GFP in the cells within the target mouse (administered to Group No. 6).

The study involved the intramuscular (IM) injection of mice on day one followed by booster injections on day 14 and 28. The mice were then taken down on day 35 and serum was collected for determination of antibody titer. Six groups of three mice were used for this experiment and the experiment was carried out twice for a total of six mice per group. The first group was a naïve control meaning that they did not receive any injections. The second group was injected with control minicells that did not have any GFP protein or GFP plasmid DNA. The third group was injected with the naked GFP plasmid alone (eukaryotic expression sequence operably linked to GFP nucleic acid). This group served as the positive control group as it is well known that IM injections of naked DNA are capable of inducing an antibody response against proteins encoded by the delivered plasmid. The fourth group was injected with minicells containing the expressed GFP protein, to determine the ability of minicells to deliver protein. The fifth group was injected with minicells containing the plasmid having a eukaryotic expression sequence operably linked to GFP nucleic acid. The final group was injected with minicells containing both the plasmid having a eukaryotic expression sequence operably linked to GFP nucleic acid, as well as the expressed GFP protein to determine if delivery of GFP protein in combination with the GFP plasmid would enhance the response. The groups are outlined in the table below. All groups were normalized to contain equal amounts of plasmid and protein.

| GROUPS OF MICE | |
| --- | --- |
| Group # | Injection |
| 1 | Naïve mice |
| 2 | Empty minicell control |
| 3 | Naked GFP plasmid DNA |
| 4 | Minicell containing GFP protein |
| 5 | Minicell containing GFP plasmid |
| 6 | Minicell containing both GFP protein and GFP Plasmid |

Following the take down of the mice, serum was collected from all mice and prepared for antibody titer analysis. Antibody titer analysis was carried out using standard ELISA techniques. Purified GFP protein was used in the ELISA as the substrate for the detection of mouse GFP antibodies and HRP conjugated anti-mouse antibodies were used to detect the anti-GFP antibodies produced by the mice. Read out was measured using an ELISA plate reader and the data was converted to titers using standard equations.

Results

As expected, the serum from groups one and two did not contain any detectable antibodies against the GFP protein. Groups three, four, and five all obtained a measurable titer and were statistically the same. All three groups were able to induce an antibody response, which indicates that the naked plasmid DNA as well as the plasmid DNA in the minicell was delivered to an in vivo target and GFP was produced, resulting in an antibody response. Surprisingly, the level of response to the minicell with a combination of both GFP protein and GFP plasmid (group 6) was much higher than all other groups. The titer was 10× the response of groups 3, 4, and 5. These data definitively demonstrate the ability of minicells to deliver plasmid DNA to an in vivo target and protein production from the plasmid upon delivery in the target cell.

What is claimed is:

1. A fully intact eubacterial minicell for use in generating an immunogenic response in an animal, comprising a plasmid having an open reading frame encoding a viral antigen of interest, and a eukaryotic expression sequence operably linked to said open reading frame, such that said antigen of interest is expressed in said animal.

2. The minicell of claim 1, wherein said eukaryotic expression sequence comprises a CMV promoter.

3. The minicell of claim 1, wherein said eukaryotic expression sequence comprises a stress inducible an inducible promoter.

4. The minicell of claim 1, wherein said open reading frame is from the genome of a virus.

5. The minicell of claim 4, where said virus is selected from the group consisting of HIV, smallpox virus, Hepatitis A, Hepatitis B, Hepatitis C, influenza virus, varicella zoster virus, Herpes Simplex Virus, adenovirus, rhinovirus, rinderpest, exhovirus, rotavirus, respiratory syncitial virus, papilloma virus, papova virus, cytomegalovirus, echinovirus, arbovirus, hantavirus, coxsackie virus, mumps virus, measles virus, polio virus, and rubella virus.

6. The minicell of claim 1, further comprising a prokaryotic expression sequence operably linked to said open reading frame, such that said antigen of interest is expressed in the minicell and the animal.

7. The minicell of claim 6, wherein said antigen of interest expressed in the minicell is displayed on the surface of the minicell.

* * * * *

SEQUENCE LISTING

<160> NUMBER OF SEQ ID NOS: 2

<210> SEQ ID NO 1
<211> LENGTH: 6085
<212> TYPE: DNA
<213> ORGANISM: Artificial Sequence
<220> FEATURE:
<223> OTHER INFORMATION: Expression Plasmid

<400> SEQUENCE: 1

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccaa | gcttaattaa | tctttctgcg | 420 |
| aattgagatg | acgccactgg | ctgggcgtca | tcccggtttc | ccgggtaaac | accaccgaaa | 480 |
| aatagttact | atcttcaaag | ccacattcgg | tcgaaatatc | actgattaac | aggcggctat | 540 |
| gctggagaag | atattgcgca | tgacacactc | tgacctgtcg | cagatattga | ttgatggtca | 600 |
| ttccagtctg | ctggcgaaat | tgctgacgca | aaacgcgctc | actgcacgat | gcctcatcac | 660 |
| aaaatttatc | cagcgcaaag | ggacttttca | ggctagccgc | cagccgggta | atcagcttat | 720 |
| ccagcaacgt | ttcgctggat | gttggcggca | acgaatcact | ggtgtaacga | tggcgattca | 780 |
| gcaacatcac | caactgcccg | aacagcaact | cagccatttc | gttagcaaac | ggcacatgct | 840 |
| gactactttc | atgctcaagc | tgaccgataa | cctgccgcgc | ctgcgccatc | ccatgctac | 900 |
| ctaagcgcca | gtgtggttgc | cctgcgctgg | cgttaaatcc | cggaatcgcc | cctgccagt | 960 |
| caagattcag | cttcagacgc | tccgggcaat | aaataatatt | ctgcaaaacc | agatcgttaa | 1020 |
| cggaagcgta | ggagtgttta | tcgtcagcat | gaatgtaaaa | gagatcgcca | cgggtaatgc | 1080 |
| gataagggcg | atcgttgagt | acatgcaggc | cattaccgcg | ccagacaatc | accagctcac | 1140 |
| aaaaatcatg | tgtatgttca | gcaaagacat | cttgcggata | acggtcagcc | acagcgactg | 1200 |
| cctgctggtc | gctggcaaaa | aaatcatctt | tgagaagttt | taactgatgc | gccaccgtgg | 1260 |
| ctacctcggc | cagagaacga | agttgattat | tcgcaatatg | gcgtacaaat | acgttgagaa | 1320 |
| gattcgcgtt | attgcagaaa | gccatcccgt | ccctggcgaa | tatcacgcgg | tgaccagtta | 1380 |
| aactctcggc | gaaaaagcgt | cgaaaagtgg | ttactgtcgc | tgaatccaca | gcgataggcg | 1440 |
| atgtcagtaa | cgctggcctc | gctgtggcgt | agcagatgtc | gggctttcat | cagtcgcagg | 1500 |
| cggttcaggt | atcgctgagg | cgtcagtccc | gtttgctgct | taagctgccg | atgtagcgta | 1560 |
| cgcagtgaaa | gagaaaattg | atccgccacg | gcatcccaat | tcacctcatc | ggcaaaatgg | 1620 |
| tcctccagcc | aggccagaag | caagttgaga | cgtgatgcgc | tgttttccag | gttctcctgc | 1680 |
| aaactgcttt | tacgcagcaa | gagcagtaat | tgcataaaca | agatctcgcg | actggcggtc | 1740 |
| gagggtaaat | cattttcccc | ttcctgctgt | tccatctgtg | caaccagctg | tcgcacctgc | 1800 |
| tgcaatacgc | tgtggttaac | gcgccagtga | gacggatact | gcccatccag | ctcttgtggc | 1860 |
| agcaactgat | tcagcccggc | gagaaactga | atcgatccg | gcgagcgata | cagcacattg | 1920 |
| gtcagacaca | gattatcggt | atgttcatac | agatgccgat | catgatcgcg | tacgaaacag | 1980 |

-continued

| | |
|---|---|
| accgtgccac cggtgatggt atagggctgc ccattaaaca catgaatacc cgtgccatgt | 2040 |
| tcgacaatca caatttcatg aaaatcatga tgatgttcag gaaaatccgc ctgcgggagc | 2100 |
| cggggttcta tcgccacgga cgcgttacca gacggaaaaa aatccacact atgtaatacg | 2160 |
| gtcatactgg cctcctgatg tcgtcaacac ggcgaaatag taatcacgag gtcaggttct | 2220 |
| taccttaaat tttcgacgga aaaccacgta aaaaacgtcg attttttcaag atacagcgtg | 2280 |
| aattttcagg aaatgcggtg agcatcacat caccacaatt cagcaaattg tgaacatcat | 2340 |
| cacgttcatc tttccctggt tgccaatggc ccattttcct gtcagtaacg agaaggtcgc | 2400 |
| gaattcaggc gcttttttaga ctggtcgtaa tgaaattcag gaggttgctc taatgatgat | 2460 |
| tactctgcgc aaacttcctc tggcggttgc cgtcgcagcg ggcgtaatgt ctgctcaggc | 2520 |
| aatggctgtt gatttccacg gctatgcacg ttccggtatt ggttggacag gtagcggcgg | 2580 |
| tgaacaacag tgtttccaga ctaccggtgc tcaaagtaaa taccgtcttg gcaacgaatg | 2640 |
| tgaaacttat gctgaattaa aattgggtca ggaagtgtgg aaagagggcg ataagagctt | 2700 |
| ctatttcgac actaacgtgg cctattccgt cgcacaacag aatgactggg aagctaccga | 2760 |
| tccggccttc cgtgaagcaa acgtgcaggg taaaaacctg atcgaatggc tgccaggctc | 2820 |
| caccatctgg gcaggtaagc gcttctacca acgtcatgac gttcatatga tcgacttcta | 2880 |
| ctactgggat atttctggtc ctggtgccgg tctcgagtct agactggaaa acatcgatgt | 2940 |
| tggcttcggt aaactctctc tggcagcaac ccgctcctct gaagctggtg gttcttcctc | 3000 |
| tttcgccagc aacaatattt atgactatac caacgaaacc gcgaacgacg ttttcgatgt | 3060 |
| gcgtttagcg cagatggaaa tcaacccggg cggcacatta gaactgggtg tcgactacgg | 3120 |
| tcgtgccaac ttgcgtgata actatcgtct ggttgatggc gcatcgaaag acggctggtt | 3180 |
| attcactgct gaacatactc agagtgtcct gaagggcttt aacaagtttg ttgttcagta | 3240 |
| cgctactgac tcgatgacct cgcagggtaa agggctgtcg cagggttctg gcgttgcatt | 3300 |
| tgataacgaa aaatttgcct acaatatcaa caacaacggt cacatgctgc gtatcctcga | 3360 |
| ccacggtgcg atctccatgg gcgacaactg gacatgatg tacgtgggta tgtaccagga | 3420 |
| tatcaactgg gataacgaca acggcaccaa gtggtggacc gtcggtattc gcccgatgta | 3480 |
| caagtggacg ccaatcatga gcaccgtgat ggaaatcggc tacgacaacg tcgaatccca | 3540 |
| gcgcaccggc gacaagaaca atcagtacaa aattaccctc gcacaacaat ggcaggctgg | 3600 |
| cgacagcatc tggtcacgcc cggctattcg tgtcttcgca acctacgcca gtgggatga | 3660 |
| gaaatggggt tacgactaca ccggtaacgc tgataacaac gcgaacttcg gcaaagccgt | 3720 |
| tcctgctgat ttcaacggcg gcagcttcgg tcgtggcgac agcgacgagt ggaccttcgg | 3780 |
| tgcccagatg gaaatctggt ggtaaatccc cgcgccctca tccgaagggg cgtattggta | 3840 |
| ccgagctcga attcgtaatc atggtcatag ctgtttcctg tgtgaaattg ttatccgctc | 3900 |
| acaattccac acaacatacg agccggaagc ataaagtgta aagcctgggg tgcctaatga | 3960 |
| gtgagctaac tcacattaat tgcgttgcgc tcactgcccg ctttccagtc gggaaacctg | 4020 |
| tcgtgccagc tgcattaatg aatcggccaa cgcgcgggga gaggcggttt gcgtattggg | 4080 |
| cgctcttccg cttcctcgct cactgactcg ctgcgctcgg tcgttcggct gcggcgagcg | 4140 |
| gtatcagctc actcaaaggc ggtaatacgg ttatccacag aatcaggga taacgcagga | 4200 |
| aagaacatgt gagcaaaagg ccagcaaaag gccaggaacc gtaaaaaggc cgcgttgctg | 4260 |
| gcgttttttcc ataggctccg ccccctgac gagcatcaca aaaatcgacg ctcaagtcag | 4320 |
| aggtggcgaa acccgacagg actataaaga taccaggcgt ttccccctgg aagctccctc | 4380 |

```
gtgcgctctc ctgttccgac cctgccgctt accggatacc tgtccgcctt tctcccttcg    4440
ggaagcgtgg cgctttctca tagctcacgc tgtaggtatc tcagttcggt gtaggtcgtt    4500
cgctccaagc tgggctgtgt gcacgaaccc cccgttcagc ccgaccgctg cgccttatcc    4560
ggtaactatc gtcttgagtc caacccggta agacacgact tatcgccact ggcagcagcc    4620
actggtaaca ggattagcag agcgaggtat gtaggcggtg ctacagagtt cttgaagtgg    4680
tggcctaact acggctacac tagaaggaca gtatttggta tctgcgctct gctgaagcca    4740
gttaccttcg gaaaaagagt tggtagctct tgatccggca acaaaccac cgctggtagc     4800 ggtggttttt tgtttgcaa gcagcagatt acgcgcagaa aaaaggatc tcaagaagat      4860 ccttttgatct tttctacggg gtctgacgct cagtggaacg aaaactcacg ttaagggatt    4920
ttggtcatga gattatcaaa aaggatcttc acctagatcc ttttaaatta aaaatgaagt    4980
tttaaatcaa tctaaagtat atatgagtaa acttggtctg acagttacca atgcttaatc    5040
agtgaggcac ctatctcagc gatctgtcta tttcgttcat ccatagttgc ctgactcccc    5100
gtcgtgtaga taactacgat acgggagggc ttaccatctg gccccagtgc tgcaatgata    5160
ccgcgagacc cacgctcacc ggctccagat ttatcagcaa taaaccagcc agccggaagg    5220
gccgagcgca gaagtggtcc tgcaacttta tccgcctcca tccagtctat taattgttgc    5280
cgggaagcta gagtaagtag ttcgccagtt aatagtttgc gcaacgttgt tgccattgct    5340
acaggcatcg tggtgtcacg ctcgtcgttt ggtatggctt cattcagctc cggttcccaa    5400
cgatcaaggc gagttacatg atcccccatg ttgtgcaaaa aagcggttag ctccttcggt    5460
cctccgatcg ttgtcagaag taagttggcc gcagtgttat cactcatggt tatggcagca    5520
ctgcataatt ctcttactgt catgccatcc gtaagatgct tttctgtgac tggtgagtac    5580
tcaaccaagt cattctgaga atagtgtatg cggcgaccga gttgctcttg cccggcgtca    5640
atacgggata taccgcgcc acatagcaga actttaaaag tgctcatcat tggaaaacgt     5700
tcttcggggc gaaaactctc aaggatctta ccgctgttga tccagttc gatgtaaccc      5760 actcgtgcac ccaactgatc ttcagcatct tttactttca ccagcgtttc tgggtgagca    5820
aaaacaggaa ggcaaaatgc cgcaaaaaag gaataagggc gacacggaa atgttgaata    5880 ctcatactct ccttttttca atattattga agcatttatc agggttattg tctcatgagc    5940
ggatacatat ttgaatgtat ttagaaaaat aaacaaatag gggttccgcg cacatttccc    6000
cgaaaagtgc cacctgacgt ctaagaaacc attattatca tgacattaac ctataaaaat    6060
aggcgtatca cgaggccctt tcgtc                                          6085

<210> SEQ ID NO 2
<211> LENGTH: 4812
<212> TYPE: DNA
<213> ORGANISM: Artificial Sequence
<220> FEATURE:
<223> OTHER INFORMATION: Expression Plasmid

<400> SEQUENCE: 2
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
```

-continued

```
tttcccagtc acgacgttgt aaaacgacgg ccagtgccaa gcttaattaa tctttctgcg    420
aattgagatg acgccactgg ctgggcgtca tcccggtttc ccgggtaaac accaccgaaa    480
aatagttact atcttcaaag ccacattcgg tcgaaatatc actgattaac aggcggctat    540
gctggagaag atattgcgca tgacacactc tgacctgtcg cagatattga ttgatggtca    600
ttccagtctg ctggcgaaat tgctgacgca aaacgcgctc actgacgat gcctcatcac     660
aaaatttatc cagcgcaaag ggacttttca ggctagccgc cagccgggta atcagcttat    720
ccagcaacgt ttcgctggat gttggcggca acgaatcact ggtgtaacga tggcgattca    780
gcaacatcac caactgcccg aacagcaact cagccatttc gttagcaaac ggcacatgct    840
gactactttc atgctcaagc tgaccgataa cctgccgcgc ctgcgccatc ccatgctac     900
ctaagcgcca gtgtggttgc cctgcgctgg cgttaaatcc cggaatcgcc cctgccagt     960
caagattcag cttcagacgc tccgggcaat aaataatatt ctgcaaaacc agatcgttaa   1020
cggaagcgta ggagtgttta tcgtcagcat gaatgtaaaa gagatcgcca cgggtaatgc   1080
gataagggcg atcgttgagt acatgcaggc cattaccgcg ccagacaatc accagctcac   1140
aaaaatcatg tgtatgttca gcaaagacat cttgcggata acggtcagcc acagcgactg   1200
cctgctggtc gctggcaaaa aaatcatctt tgagaagttt taactgatgc gccaccgtgg   1260
ctacctcggc cagagaacga agttgattat tcgcaatatg gcgtacaaat acgttgagaa   1320
gattcgcgtt attgcagaaa gccatcccgt ccctggcgaa tatcacgcgg tgaccagtta   1380
aactctcggc gaaaagcgt cgaaaagtgg ttactgtcgc tgaatccaca gcgataggcg    1440
atgtcagtaa cgctggcctc gctgtggcgt agcagatgtc gggctttcat cagtcgcagg   1500
cggttcaggt atcgctgagg cgtcagtccc gtttgctgct taagctgccg atgtagcgta   1560
cgcagtgaaa gagaaaattg atccgccacg gcatcccaat tcacctcatc ggcaaaatgg   1620
tcctccagcc aggccagaag caagttgaga cgtgatgcgc tgttttccag gttctcctgc   1680
aaactgcttt tacgcagcaa gagcagtaat tgcataaaca agatctcgcg actggcggtc   1740
gagggtaaat cattttcccc ttcctgctgt tccatctgtg caaccagctg tcgcacctgc   1800
tgcaatacgc tgtggttaac gcgccagtga acggatact gcccatccag ctcttgtggc    1860
agcaactgat tcagcccggc gagaaactga atcgatccg gcgagcgata cagcacattg    1920
gtcagacaca gattatcggt atgttcatac agatgccgat catgatcgcg tacgaaacag   1980
accgtgccac cggtgatggt atagggctgc ccattaaaca catgaatacc cgtgccatgt   2040
tcgacaatca caatttcatg aaaatcatga tgatgttcag gaaaatccgc ctgcgggagc   2100
cggggttcta tcgccacgga cgcgttacca gacggaaaaa aatccacact atgtaatacg   2160
gtcatactgg cctcctgatg tcgtcaacac ggcgaaatag taatcacgag gtcaggttct   2220
taccttaaat tttcgacgga aaaccacgta aaaaacgtcg attttttcaag atacagcgtg   2280
aattttcagg aaatgcggtg agcatcacat caccacaatt cagcaaattg tgaacatcat   2340
cacgttcatc tttccctggt tgccaatggc ccattttcct gtcagtaacg agaaggtcgc   2400
gaattcaggc gcttttttaga ctggtcgtaa tgaaattcag gaggttgctc taatgaactt   2460
ggggaatcga ctgtttattc tgatagcggt cttacttccc ctcgcagtat tactgctcgt   2520
cgactctaga ggatccccgc gccctcatcc gaaagggcgt attggtaccg agctcgaatt   2580
cgtaatcatg gtcatagctg tttcctgtgt gaaattgtta tccgctcaca attccacaca   2640
acatacgagc cggaagcata aagtgtaaag cctggggtgc ctaatgagtg agctaactca   2700
cattaattgc gttgcgctca ctgcccgctt tccagtcggg aaacctgtcg tgccagctgc   2760
```

```
attaatgaat cggccaacgc gcggggagag gcggtttgcg tattgggcgc tcttccgctt    2820
cctcgctcac tgactcgctg cgctcggtcg ttcggctgcg gcgagcggta tcagctcact    2880
caaaggcggt aatacggtta tccacagaat caggggataa cgcaggaaag aacatgtgag    2940
caaaaggcca gcaaaaggcc aggaaccgta aaaaggccgc gttgctggcg ttttccata     3000
ggctccgccc ccctgacgag catcacaaaa atcgacgctc aagtcagagg tggcgaaacc    3060
cgacaggact ataaagatac caggcgtttc ccctggaag ctccctcgtg cgctctcctg     3120
ttccgaccct gccgcttacc ggatacctgt ccgcctttct cccttcggga agcgtggcgc    3180
tttctcatag ctcacgctgt aggtatctca gttcggtgta ggtcgttcgc tccaagctgg    3240
gctgtgtgca cgaaccccc gttcagcccg accgctgcgc cttatccggt aactatcgtc     3300
ttgagtccaa cccggtaaga cacgacttat cgccactggc agcagccact ggtaacagga    3360
ttagcagagc gaggtatgta ggcggtgcta cagagttctt gaagtggtgg cctaactacg    3420
gctacactag aaggacagta tttggtatct gcgctctgct gaagccagtt accttcggaa    3480
aaagagttgg tagctcttga tccggcaaac aaaccaccgc tggtagcggt ggtttttttg    3540
tttgcaagca gcagattacg cgcagaaaaa aaggatctca agaagatcct ttgatctttt    3600
ctacggggtc tgacgctcag tggaacgaaa actcacgtta agggatttg gtcatgagat     3660
tatcaaaaag gatcttcacc tagatccttt taaattaaaa atgaagtttt aaatcaatct    3720
aaagtatata tgagtaaact tggtctgaca gttaccaatg cttaatcagt gaggcaccta    3780
tctcagcgat ctgtctattt cgttcatcca tagttgcctg actccccgtc gtgtagataa    3840
ctacgatacg ggagggctta ccatctggcc ccagtgctgc aatgataccg cgagacccac    3900
gctcaccggc tccagattta tcagcaataa accagccagc cggaagggcc gagcgcagaa    3960
gtggtcctgc aactttatcc gcctccatcc agtctattaa ttgttgccgg gaagctagag    4020
taagtagttc gccagttaat agtttgcgca acgttgttgc cattgctaca ggcatcgtgg    4080
tgtcacgctc gtcgtttggt atggcttcat tcagctccgg ttcccaacga tcaaggcgag    4140
ttacatgatc ccccatgttg tgcaaaaaag cggttagctc cttcggtcct ccgatcgttg    4200
tcagaagtaa gttggccgca gtgttatcac tcatggttat ggcagcactg cataattctc    4260
ttactgtcat gccatccgta agatgctttt ctgtgactgg tgagtactca accaagtcat    4320
tctgagaata gtgtatgcgg cgaccgagtt gctcttgccc ggcgtcaata cgggataata    4380
ccgcgccaca tagcagaact ttaaaagtgc tcatcattgg aaaacgttct cggggcgaa     4440
aactctcaag gatcttaccg ctgttgagat ccagttcgat gtaacccact cgtgcaccca    4500
actgatcttc agcatctttt actttcacca gcgtttctgg gtgagcaaaa acaggaaggc    4560
aaaatgccga aaaaaggga ataagggcga cacggaaatg ttgaatactc atactcttcc    4620
ttttcaata ttattgaagc atttatcagg gttattgtct catgagcgga tacatatttg     4680
aatgtattta gaaaaataaa caatagggg ttccgcgcac atttccccga aaagtgccac     4740
ctgacgtcta agaaaccatt attatcatga cattaaccta taaaaatagg cgtatcacga    4800
ggccctttcg tc                                                        4812
```